United States Patent [19]

Shofner et al.

[11] Patent Number: 5,410,401

[45] Date of Patent: Apr. 25, 1995

[54] METHODS AND APPARATUS FOR MECHANICALLY AND ELECTRONICALLY CORRECTING PRESENTATION OF ENTITIES IN A FLUID FLOW

[75] Inventors: Frederick M. Shofner; Michael E. Galyon; Joseph C. Baldwin; Masood A. Khan, all of Knoxville, Tenn.

[73] Assignee: Zellweger Uster, Inc., Knoxville, Tenn.

[21] Appl. No.: 999,211

[22] Filed: Dec. 31, 1992

Related U.S. Application Data

[63] Continuation-in-part of Ser. No. 493,961, Mar. 14, 1990, Pat. No. 5,270,787.

[51] Int. Cl.⁶ .................... G01N 21/00; G01N 15/14; G01L 5/04
[52] U.S. Cl. .................... 356/238; 73/160; 356/383; 356/385
[58] Field of Search .............. 356/238, 383–384, 356/430; 19/200; 250/560; 73/160

[56] References Cited

U.S. PATENT DOCUMENTS

| | | |
|---|---|---|
| 2,829,771 | 4/1958 | Dahlstrom . |
| 3,816,001 | 6/1974 | Duncan et al. . |
| 4,027,162 | 5/1977 | Knollenberg ............... 250/345 |
| 4,511,253 | 4/1985 | Glockner et al. ............ 356/385 |
| 4,512,060 | 4/1985 | Shofner ...................... 19/200 |
| 4,527,306 | 7/1985 | Thannheiser ............... 19/66 |
| 4,631,781 | 12/1986 | Shofner ...................... 19/200 |
| 4,686,744 | 8/1987 | Shofner ...................... 19/200 |
| 4,737,648 | 4/1988 | Smith et al. ................. 356/343 X |
| 4,879,471 | 11/1989 | Dahlquist .................... 250/359 |
| 5,121,522 | 6/1992 | Leifeld et al. ............... 19/66 |
| 5,270,787 | 12/1993 | Shofner et al. ............. 356/338 |

FOREIGN PATENT DOCUMENTS

| | | | |
|---|---|---|---|
| 225009 | 6/1987 | European Pat. Off. | ........... 15/2 |
| WO89/01619 | 7/1988 | WIPO | ........... 15/14 |

OTHER PUBLICATIONS

Advanced Fiber Information System: A New Technology for Evaluating Cotton, By: Shofner, Williams, Bragg and Sasser.

Basic Investigation of the Behavior of Cotton Subjected to Aerodynamic Forces, For the Purpose of Improving The Processing Characteristics of Cotton Textiles, Tryggve Eeg–Olofsson.

*Primary Examiner*—Vincent P. McGraw
*Assistant Examiner*—K. P. Hantis

[57] ABSTRACT

An apparatus for delooping fibers in a fluid flow preferably includes a cyclone for receiving entities from a fiber individualizer and delivering individual fibers to a sensor. The fluid flow rate to the cyclone is set to optimize operation of the individualizer and the flow rate from the cyclone is set to optimize operation of the sensor. A nozzle is provided in the sensor for mechanically delooping the fibers so they are sensed in a straight condition. In addition, electronics associated with the sensor detects sensor signals corresponding to looped fibers and electronically "deloops" the fibers to produce data, such as the actual length of a fiber that was presented to the sensor in a looped condition.

19 Claims, 17 Drawing Sheets

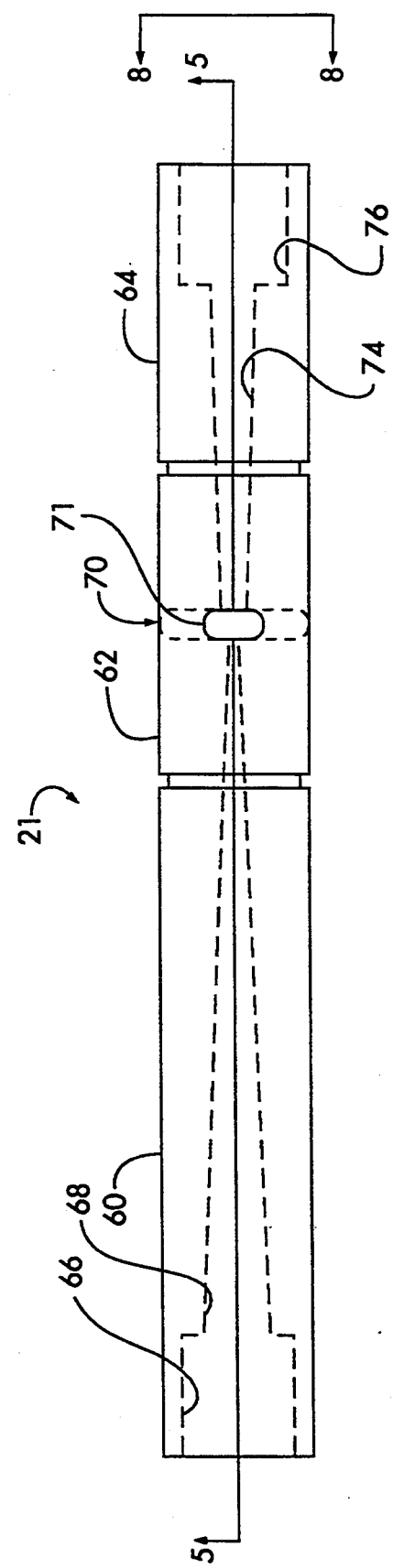

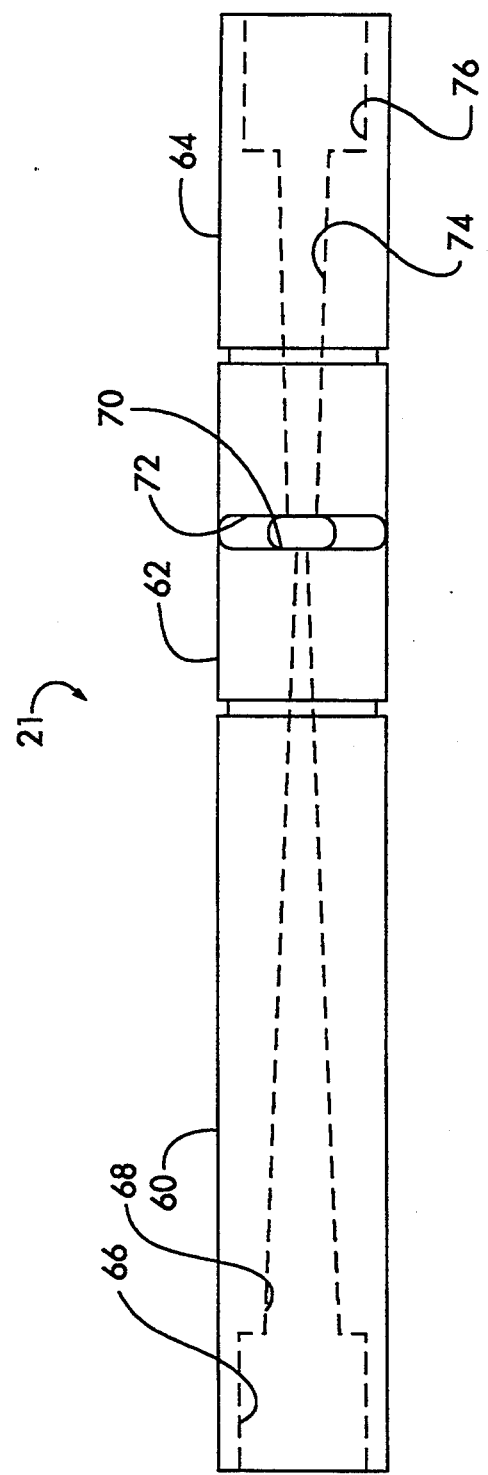

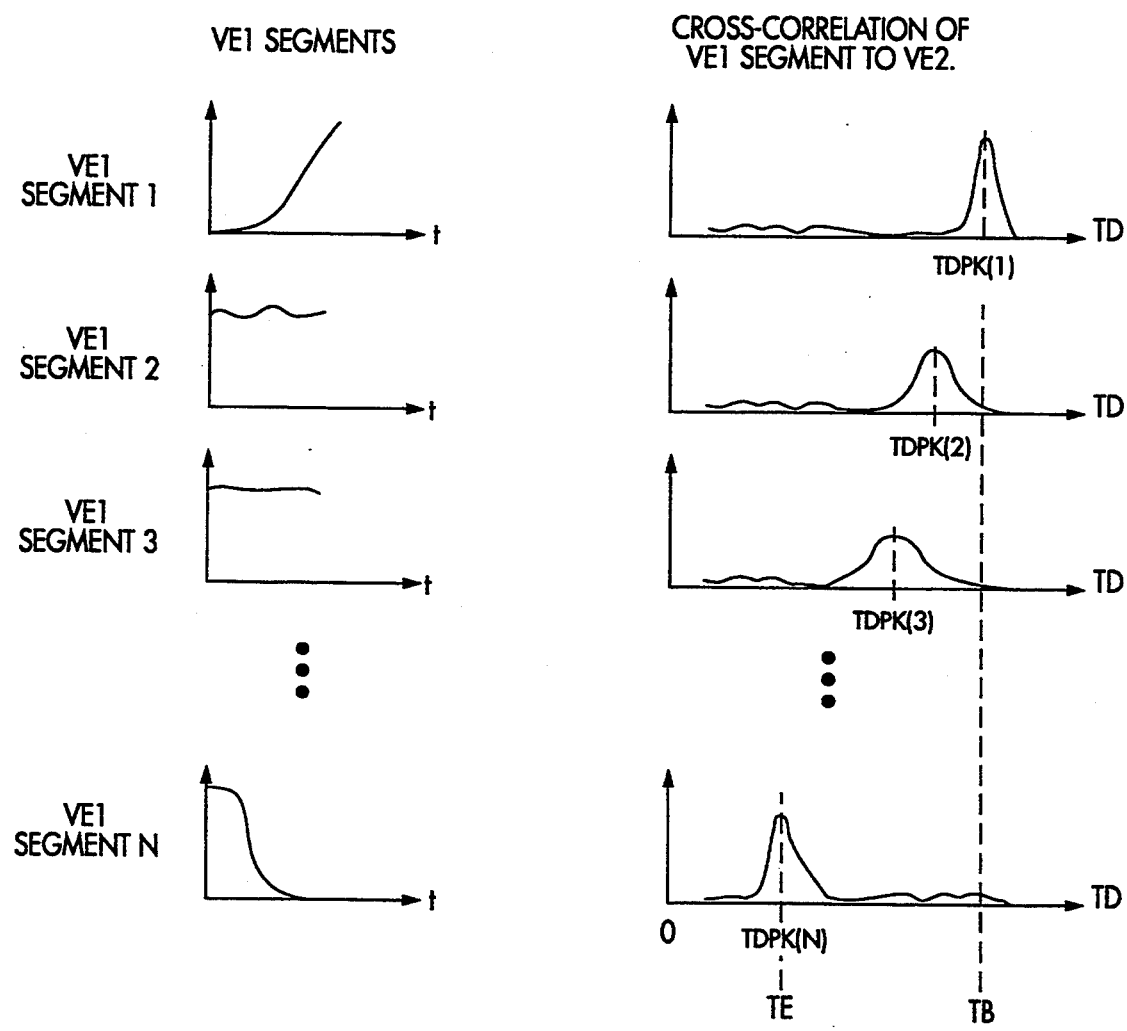

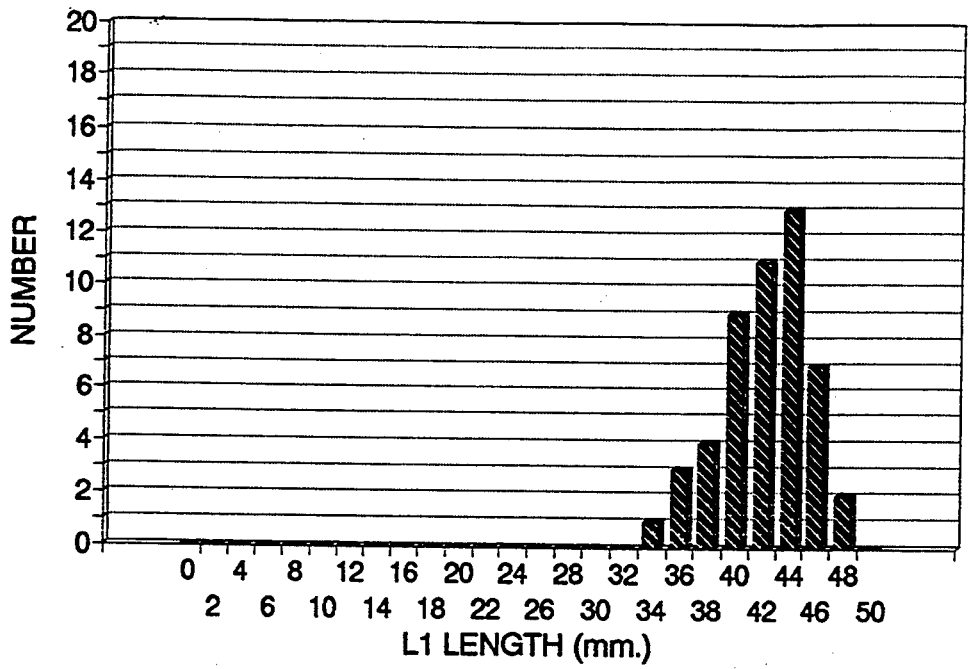
FIG. 16-A
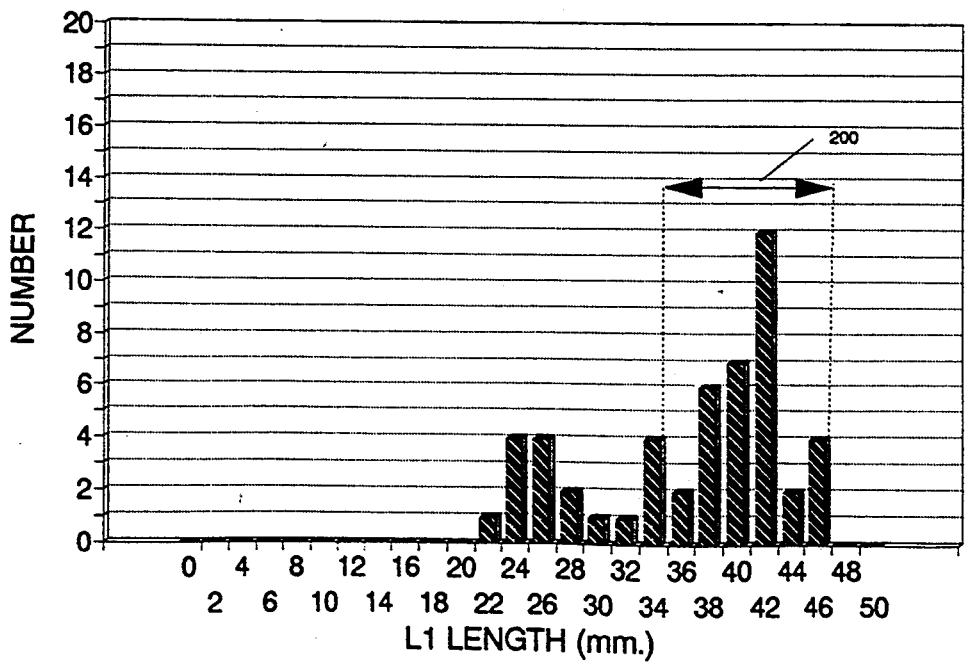
FIG. 16-B

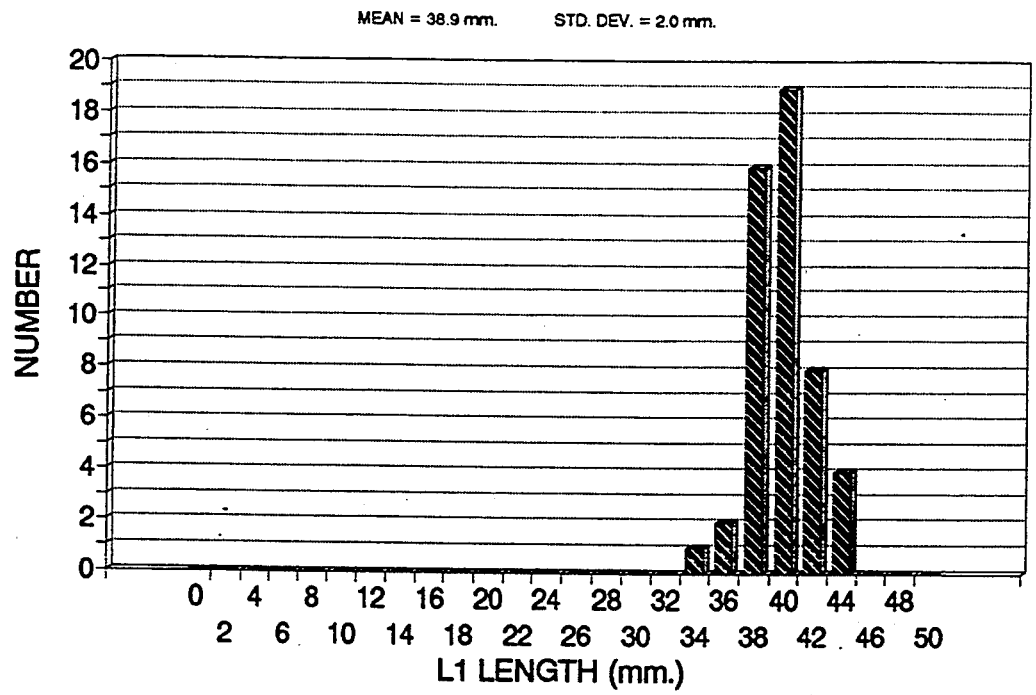
FIG. 17-A
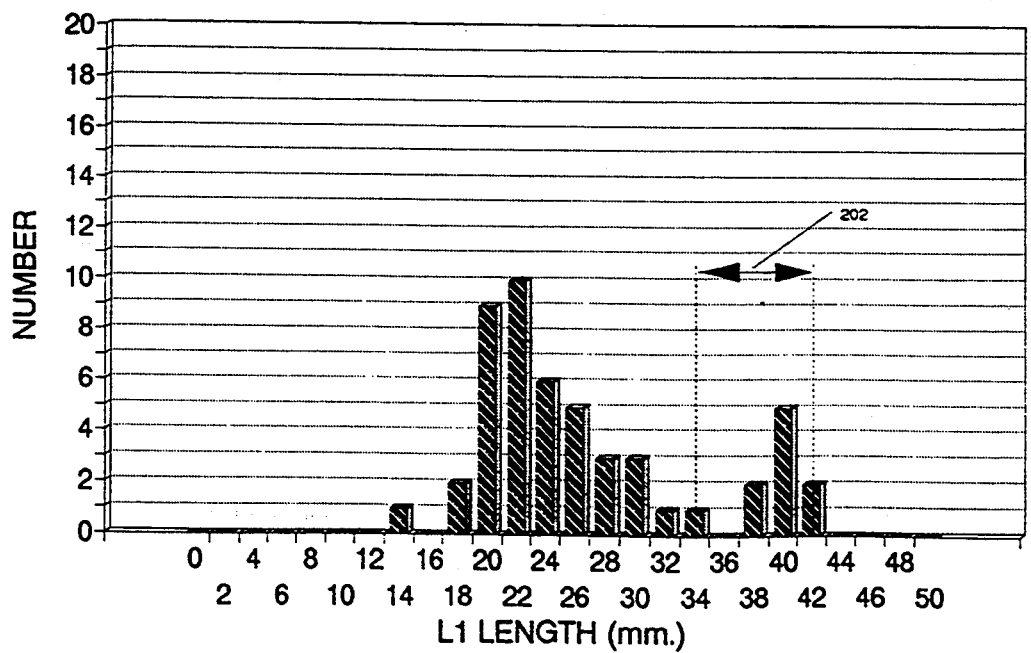
FIG. 17-B

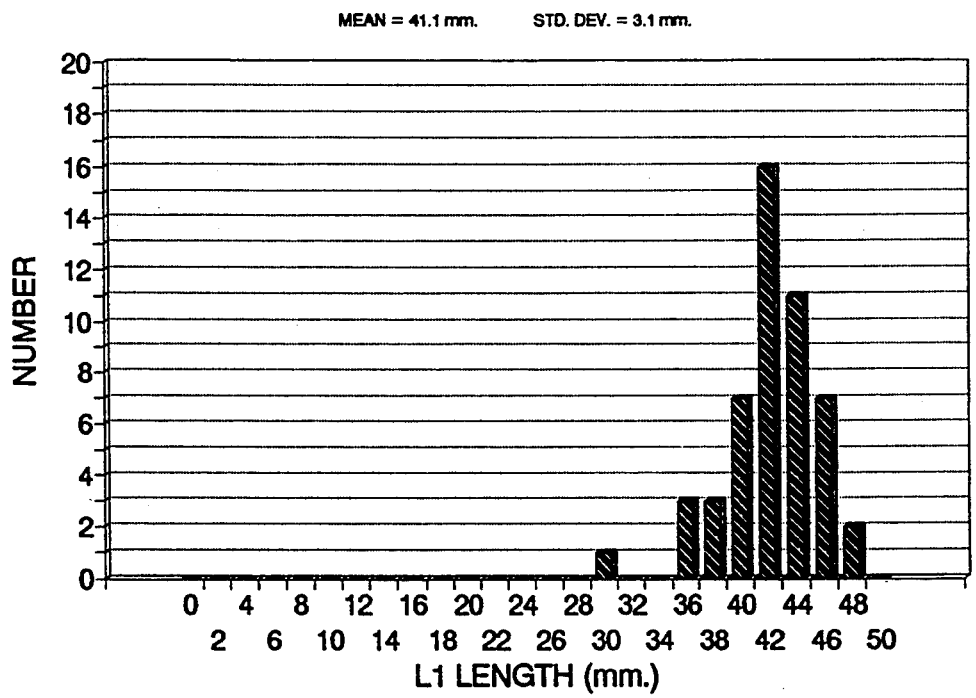
FIG. 18-A
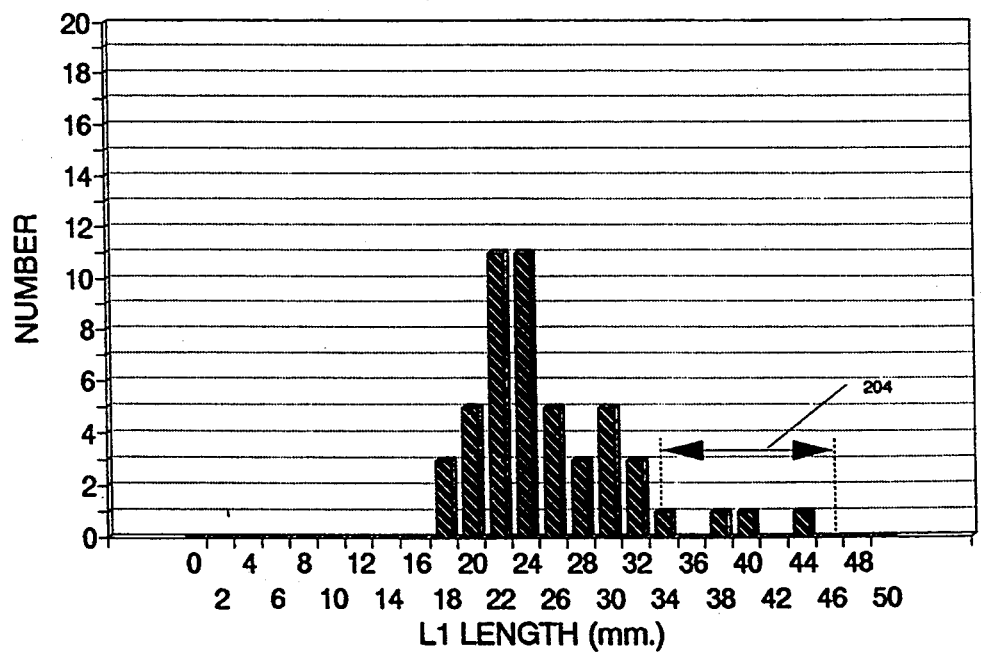
FIG. 18-B

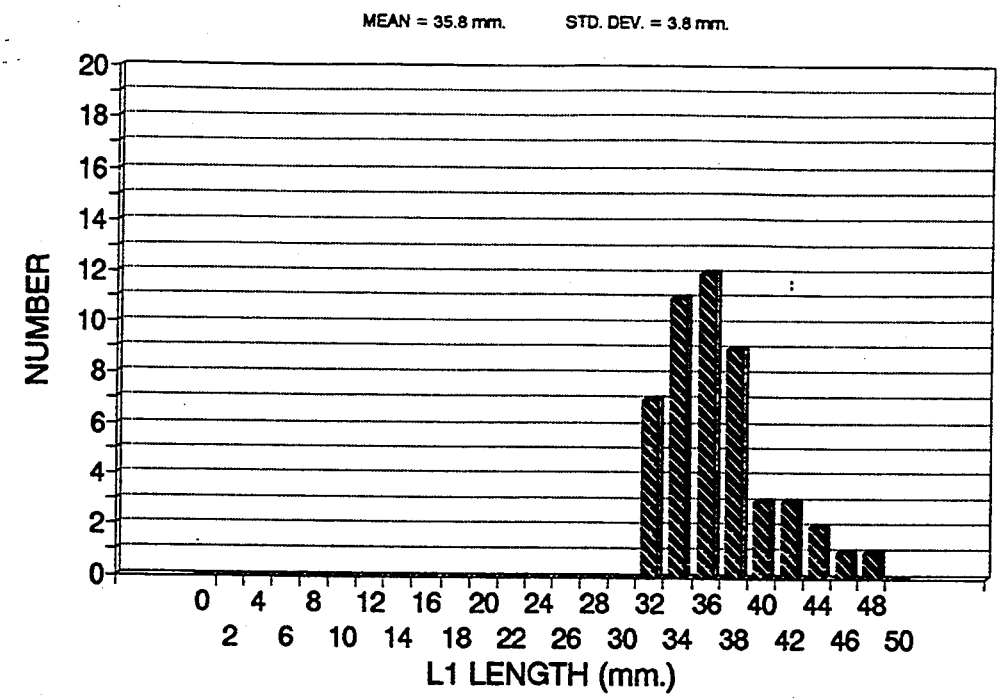
FIG. 19-A
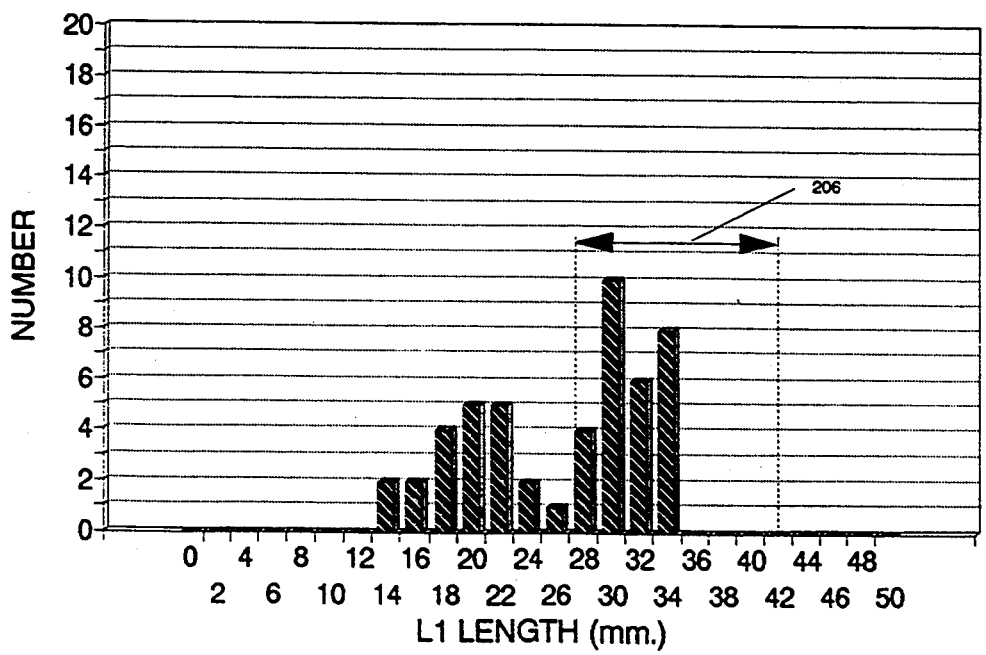
FIG. 19-B

METHODS AND APPARATUS FOR MECHANICALLY AND ELECTRONICALLY CORRECTING PRESENTATION OF ENTITIES IN A FLUID FLOW

CROSS REFERENCE TO RELATED APPLICATIONS

This application is a continuation-in-part of application Ser. No. 07/493,961 filed Mar. 14, 1990, now U.S. Pat. No. 5,270,787, issued Dec. 14, 1993, entitled "Electro-Optical Methods and Apparatus for High Speed Multivariate Measurement of Individual Entities in Fiber or Other Sample" which is incorporated herein by reference.

FIELD OF THE INVENTION

This invention relates to methods and apparatus which improve measurement and processing of individual entities transported by fluid flows such as neps, trash, and fibers. The instant invention focusses on methods and apparatus to improve individual fiber measurements, and specifically provides for generalized and improved matching of the fluid flow in and between the entity individualizer and the entity sensor(s), and further provides methods and apparatus to correct for fiber looping; that is, fluid dynamic and electronic means are provided to "deloop" them.

BACKGROUND

A fiber-testing instrument commonly known in the textile industry as AFIS (Advanced Fiber Information System) is manufactured by Zellweger Uster, Inc., Knoxville, Tennessee. This equipment in now being used world-wide as a textile process quality control tool to optimize processing machinery. Further, its value and use as a tool to optimize textile raw materials purchase and allocation is increasing. For both applications, the primary performance factors are relevance of the data products, reproducibility, testing speed, ease of use, and costs. It is not essential that the measurement be absolute. However, it was a goal from the outset to make AFIS basic and absolute. One of the fundamentally important reasons for this goal was to improve basic understandings of the fiber to yarn engineering process.

Further experience with the AFIS instrument has confirmed that it will indeed become the reference method for providing distributions of nep and trash entities. Importantly here, AFIS can become the absolute reference for distributions of fiber length, diameter, fineness, and maturity provided certain improvements are made. The primary improvement needed in the electro-optical sensor relates to fibers which are presented in a looped condition (fiber folded back on itself). Such looped fibers can be excluded from the data product on the basis of their waveform characteristics, as is done currently, but the AFIS method becomes more basic, more absolute, and faster if loops are prevented or delooped by fluid dynamic means or if looped fiber waveforms are electronically corrected. We have discovered both fluid dynamic and electronic methods for achieving these "delooping" results.

Some of the fibers delivered pneumatically to the sensor from a fiber individualizer (described in U.S. Pat. Nos. 4,512,060; 4,631,781; and 4,686,744) are known to be looped or hooked because of the nature of the pinned cylinders, carding flats, and other elements of the entity individualization process. Further, the Reynolds numbers of the transporting and accelerating flows are sometimes deep within the turbulent flow regime. Whereas such high speed flows are advantageous for testing speed and for stretching the fiber (to remove crimp), there is, in general, substantial looping of the fibers.

One objective of the present invention is to match fluid flow to a nozzle in an "AFIS" type instrument to maximize the number of entities, such as fibers, that are presented in a desired orientation. For example, the fluid flow should be selected to optimize the number of fibers that are presented to a sensor in a straight (non-looped) condition. If a fiber is presented to a sensor in a looped condition (folded back on itself), it increases the difficulty of measuring various fiber parameters, such as fiber length.

However, even with optimal flow conditions for an AFIS type sensor, a substantial number of fibers were presented to the sensor in a looped condition. Thus, an investigation was begun to improve the presentation properties of the AFIS1 nozzle following the teachings of a paper entitled "Basic Investigation of the Behavior of Cottons Subjected to Aerodynamic Forces, For the Purpose of Improving the Processing Characteristics of Cotton Textiles," Tryggve Eeg-Olofsson, Gothenburg, Sweden (January, 1969) which was found in the Roger Milliken Textile Library, Institute of Textile Technology, Charlottesville, VA 22902 (TX 262, E26, 1969). Efforts to improve the presentation characteristics of the nozzle met with little or no success, and it was eventually discovered that the teachings of the aforementioned paper were not applicable to the AFIS nozzle for unknown reasons. In fact, it was discovered that the AFIS nozzle could be improved by a design that apparently directly contradicted the teachings of the aforementioned paper, it being understood that the AFIS nozzle is necessarily different in structure and operates in a different environment for a different purpose, than the nozzles investigated in the aforementioned paper.

Even with the improved nozzle of the present invention, in combination with the matching airflow and air condition of the present invention, some looping of the fibers persisted. Thus, electronic means were developed to electronically "deloop" the fibers, as hereinafter described in greater detail.

Accordingly, it is one objective of this invention to provide flow control means by which flows in the fiber individualizer and sensor(s) can be more generally and optimally matched to improve conditions and to minimize looping and maximize data rate. It is a further objective of the invention to provide accelerating nozzle means which deloop fibers, and it is a final objective to provide electronics means to "electronically-deloop" by analyzing sensor signal waveforms produced by looped fibers.

SUMMARY OF THE INVENTION

In accordance with the present invention, an apparatus is provided for sensing characteristics of entities carried in an airflow. In the preferred embodiment, an airflow adjustment apparatus, such as a cyclone, receives the entities and the airflow and outputs the entities in a second airflow having predetermined desired characteristics, such as a predetermined airflow rate, predetermined humidity, predetermined ionic content, etc. The entities are carried in the second airflow to an entity presentation apparatus that presents the entities in a desired physical condition in a sensing volume. The entities are originally delivered to the presentation apparatus in a desired physical condition and an undesired physical condition. The entity presentation apparatus operates on the entities to increase the proportion of entities in a desired physical condition when they are presented in the sensing volume. A sensor senses the entities within the sensing volume and produces a sensor signal that is analyzed by a computer, for example, to produce output representing characteristics of the sensed entities.

In a preferred embodiment of the above described apparatus a nozzle is used as the entity presentation apparatus. Such nozzle may or may not be used in conjunction with the airflow adjustment apparatus described above. The nozzle is designed to deloop fibers that are presented to it in a looped condition. More specifically, the nozzle is dimensioned and configured to operate on and physically deloop about one-half or more of those entities that are received in a 100% looped condition. Preferably, the nozzle has an accelerating tapered passageway whose length is greater than about 3 inches and has a taper of less than about 3°. Most preferably, the tapered passageway is about 6 inches in length and produces a nozzle exit velocity on the order of 100 meters per second. In accordance with a further aspect of the present invention, the analyzing means includes means for receiving and analyzing sensor signals and for determining at least one characteristic of looped entities based on the sensor signals. In this particular embodiment, the preferred sensor is a source of light directed through a sensing volume with first and second photodetectors for sensing light that is extinguished by entities in the sensing volume. The photodetectors are preferably positioned in a side-by-side spaced apart relationship with the second photodetector being positioned downstream of the first photodetector with reference to the airflow in the sensing volume. The first and second photodetectors produce first and second sensor signals, respectively, and each sensor signal includes a waveform corresponding to sensed characteristics of entities in the sensing volume.

The analyzer (computer) identifies the beginning and the end of the first and second waveforms in the first and second sensor signals, respectively, corresponding to a sensed entity. Then, the computer compares at least a portion of the first waveform, such as a segment of the first waveform, to the second waveform and based on this comparison produces a compensated waveform that compensates for varying velocities along the length of the entity as it is sensed.

In accordance with another aspect of the preferred embodiment, the computer sorts the data corresponding to one of the waveforms to produce a sorted waveform that is a set of values ordered by their magnitude. The computer then takes the derivative of the sorted waveform and locates major peaks in the derivative of the waveform. Based on the position of the major peaks in the derivative waveform, the computer then determines the time duration of the sorted waveform corresponding to looped, unlooped, and multiply looped sections of the sensed entity. In this manner, the computer identifies a segment of the sorted waveform corresponding to a single fiber being detected in the sensed volume. It also identifies another segment of the sorted waveform corresponding to two fibers, such as a looped fiber, being present in the sensed volume. The computer further determines segments of the waveform corresponding to 3 fibers, 4 fibers, etc. appearing in the sensed volume. This condition would occur when the fiber is double looped (3 fibers), triple looped (4 fibers), etc.

BRIEF DESCRIPTION OF THE DRAWINGS

The present invention may best be understood by reference to Detailed Description of preferred embodiments when considered in conjunction with the Drawings in which:

FIG. 3 is front view of a preferred nozzle used in the present invention to present fibers for being sensed and for at least partially delooping the fibers;

FIG. 4 is back view of the nozzle shown in FIG. 3;

FIG. 10 shows graphs of VE1 segments plotted against time on the horizontal scale and corresponding cross-correlations of each VE1 segment to the entire VE2 signal with the delay time shown in the horizontal dimension;

FIG. 16A is a frequency distribution graph showing the measured length of 50 fibers that were hand dropped in a straight condition into a nozzle of the present invention;

FIG. 16B is a frequency distribution similar to that shown in FIG. 16A showing the measured length of 50 fibers that were hand dropped in a 100% looped condition into the nozzle of the present invention;

FIGS. 17A and 17B are graphs analogous to FIGS. 16A and 16B showing frequency distribution for straight dropped fibers and 100% looped fibers dropped into an AFIS1 nozzle;

FIGS. 18A and 18B are graphs analogous to FIGS. 16A and 16B for an AFIS0 nozzle; and FIGS. 19A and 19B are graphs analogous to FIGS. 16A and 16B for a Fifteen Degree (15°) nozzle.

DETAILED DESCRIPTION

Fluid Flow and Condition Matching

Figure 1:
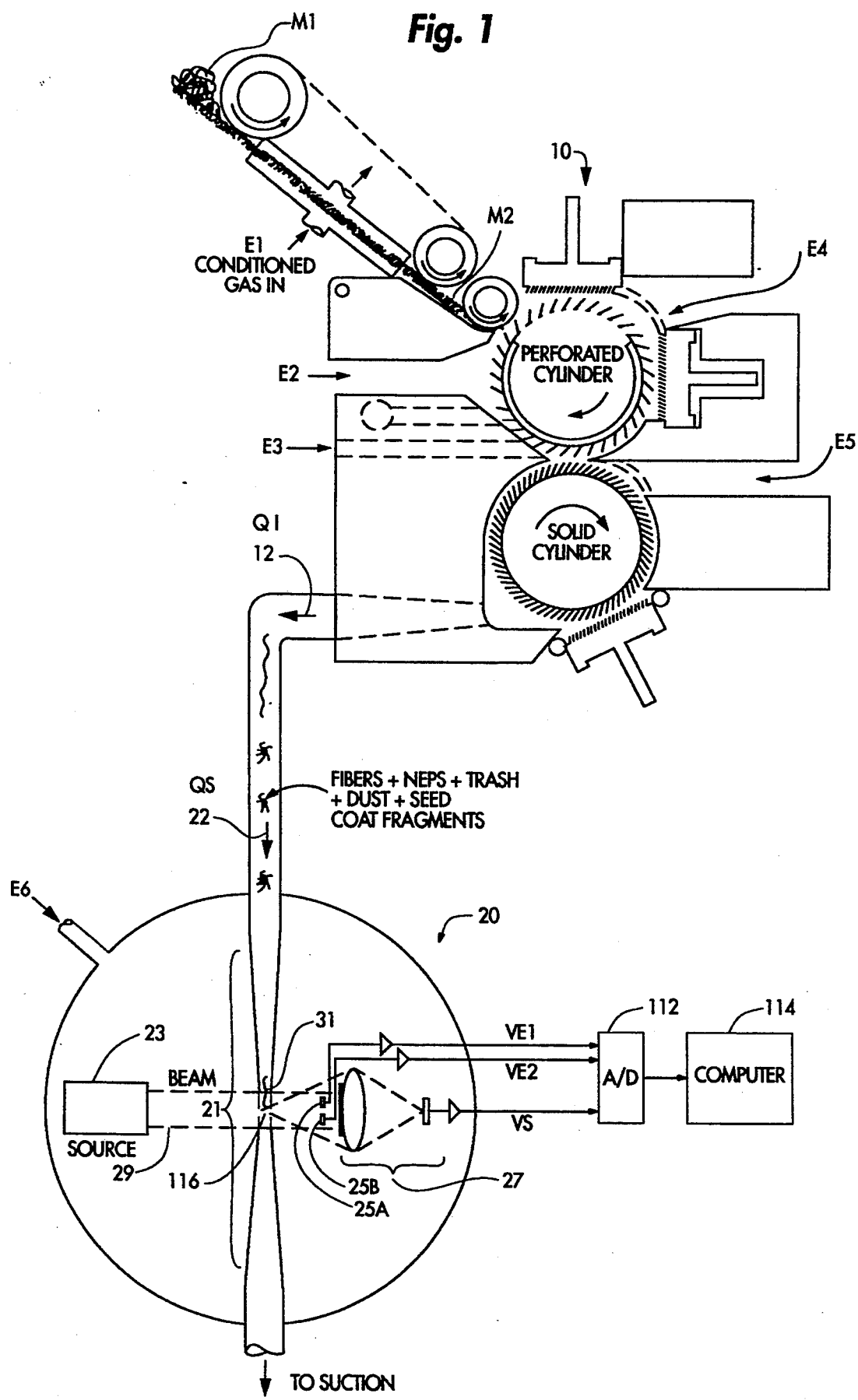
FIG. 1 is a diagrammatic overview of an apparatus for individualizing and sensing fibers, which represents one embodiment of the present invention.

Referring now to the figures in which like reference characters designate like or corresponding parts throughout the several views, preferred embodiments are described. FIG. 1 shows an entity individualizer 10 directly connected to an electro optical sensor 20. In this case, the flow 12 (QI) out of the entity individualizer 10 is identical with the flow 22 (QS) into the sensor 20. In general, it is preferable that the volumetric flow rates be different. Further, it is preferable in general that the fluid conditions within the individualizer 10 be different from those within the sensor 20. By fluid conditions, it is meant all relevant parameters which describe the fluid such as humidity, temperature, velocity, pressure, velocity fluctuations, pressure fluctuations, gas compositions, free charge concentration, static charge, radioactive particle concentration, and the like (See U.S. Pat. No. 4,631,781; Conditioned Gas is admitted in the individualizer 10 at environmental control points E1-E5 and into the Sensor 20 at E6.)

Figure 2A:
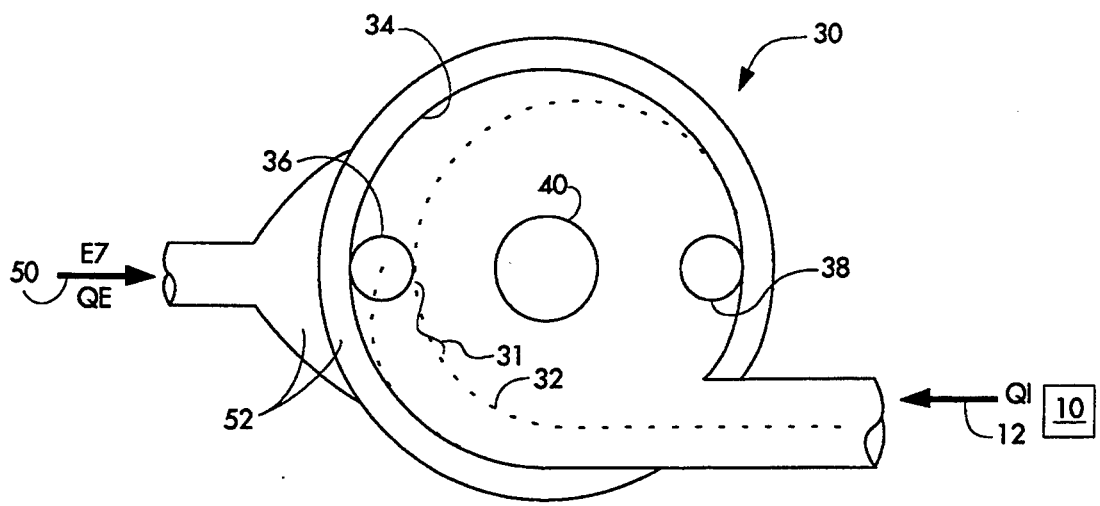
FIGS. 2A and 2B are top views and side views, respectively, of a flow matching cyclone that may be interposed between a fiber individualizer and a fiber sensor of the present invention.
Figure 2B:
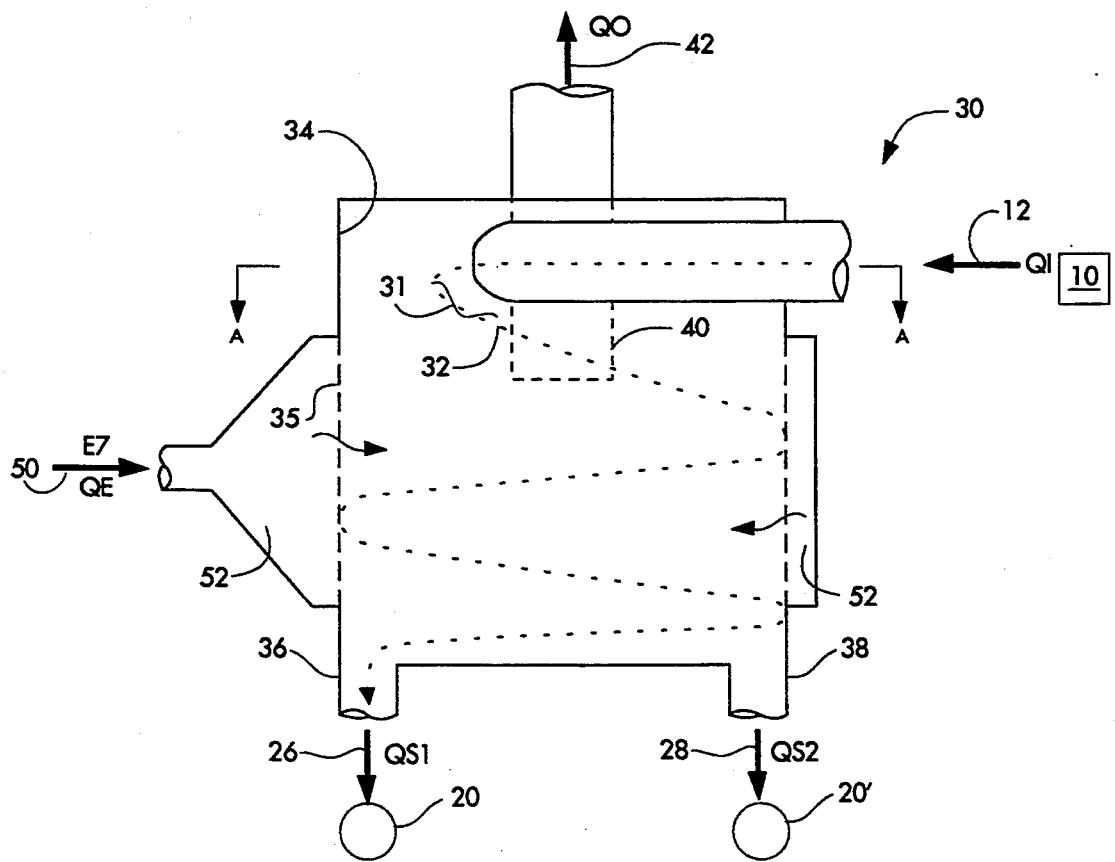

FIGS. 2A and 2B show somewhat diagrammatical top and side views, respectively, of a modified cyclone apparatus 30 which enables general matching of fluid flow rates and conditions between the entity individualizer 10 and electro-optical sensors 20 and 20' (sensor 20' being substantially the same as sensor 20 as best shown in FIG. 1). Apparatus 30 is designated as a fluid flow/-condition matching cyclone. An embodiment is illustrated which has several flow and condition matching provisions but any one of its provisions can be used with or without the others. Also, one inlet flow 12 (QI) is illustrated but several can be used. The operation of fluid flow and condition matching cyclone apparatus 30 is best understood by considering first the trajectory 32 of a typical entity 31 such as fiber, nep, or trash entity being transported into the apparatus 30 by flow 12. Centrifugal forces cause the entities 31 to move radially outward, toward the cyclone wall 34, and fluid flow and gravity cause the downward motion. Ultimately the entity 31 is transported out of the fluid/condition matching cyclone entity outlets 36 and 38 by two sensor flows 26 and 28, as illustrated in FIG. 2B.

Whereas the entities move toward the cyclone wall 34 and entity outlets 36, 38, the inlet fluid flow 12 (QI) can move to the fluid outlet 40, to the entity outlets 36, 38, or even to the perforated wall section 35, depending on the magnitude and direction of each of the flows. Consider first that the perforated wall 35 is replaced with (and now represents) a solid wall and the entity outlet flows 26 and 28 (QS1 and QS2) are reduced to zero by conventional fluid flow control means, such as air valves, which are represented in FIGS. 2A and 2B by outlets 36 and 38. Then flow 42 (QO)=flow 12 (QI), as in a simple cyclone. The entities 31 move to the bottom of the cyclone and either rotate, being driven by the normal spinning flow in the cyclone, or come to rest.

Consider next that the entity outlet flows 26 and 28 increase but remain much less than flow 12 or flow 42. Representative design values are flow 12 (QI)=10 CFM (cubic feet per min), flow 42 (QO)=8 CFM, flow 26 (QS1)+flow 28 (QS2)=2 CFM. In this manner the fluid dynamic separation of the entities 31 is approximately independent of the entity outlet flow 42. A representative design value for the aerodynamic size cutoff of the cyclone is 15 μm particles, which will move to the wall 34, and those whose aerodynamic size is smaller than 15 μm will move to the fluid outlet 40. Entities 31 of interest here fibers, neps, trash—have aerodynamic size larger than 15 μm.

Since flow 26 (QS1)+flow 28 (QS2)<<flow 12 (QI), this means that these flows can be adjusted as desired to independently match flow requirements of individualizer 10 and one or more sensors 20.

Consider now that the perforated wall 35 is in place. A conventional perforated metal wall should be smooth and have opening size about 50 μm and open area fraction about 20%. In some special cases, it is desirable to use woven metal or plastic mesh. In others, thick perforated metal with holes whose axis is inclined to the normal at about 30° can be used to facilitate maintaining the "spin" of the fluid near the outer wall and near the bottom. In all cases, an environmentally controlled gas 50 (E7) enters a plenum 52 and is distributed through the perforated wall 35. This inward flow 50 displaces at least part of the inlet flow 12 with the first result that the entities 31 move downward in fluid that increasingly has the properties and conditions of flow 50 (QE), as introduced at E7. The second result is that flow 50 adds to flows 26 and 28. This means that sensor 20 operating requirements of higher flows or different conditions can be matched almost independently of the requirement of the entity individualizer 10.

Another feature of Flow and Condition Matching Cyclone 30 is its operation as a stilling or storage chamber. That is, entities 31 can reside in a preferred environment inside apparatus 30 for much longer times than if they were directly transported from individualizer 10 to sensor 20, as shown in FIG. 1. Such stilling enables entities 31 to discharge static electricity accumulated during the rigorous individualization process. In other cases, allowing the fibers to relax in the preferred environment facilitates later testing or processing. Stilling of fibers 31 within the cyclone 30 is accomplished by using the flow control means of outlets 36 and 38 to stop the flows 26 and 28.

To conclude this portion of the description, the primary provisions of the Flow/Condition Matching Cyclone apparatus 30 are seen to be:

1.) Matching Volumetric Flow Rates—Flow 12 is matched to individualizer 10, and flows 26 and 28 are matched to sensors 20 and 20' to optimize performance;

2.) Matching Fluid Condition—The condition of flow 12 is matched to individualizer 10, whereas the condition of flows 26 and 28 is matched to sensors 20 and 20';

3.) Stilling and Relaxation of entities 31 in apparatus 30 by reducing flows 26 and 28 to zero; and any or all of the three may be used.

Improved Nozzle

Referring again to FIG. 1, the sensor 20 includes a nozzle 21 for presenting an entity 31 in a proper position for being electro-optically sensed, as described in more detail in co-pending application Ser. No. 07/493,961; filed Mar. 14, 1990, now U.S. Pat. No. 5,270,787, issued Dec. 14, 1993. In the sensor 20, a source 23 of collimated light projects a light beam 29 toward the opening 71, as seen in FIG. 3 in the nozzle 21 so that it impinges on the fiber 31 in a sensing volume 116. Two extinction sensors 25a and 25b are disposed to sense light that is extinguished by the entity 31 and produce corresponding signals VE1 and VE2. A light collection and detector system 27 is disposed to sense light that is scattered by the entity 31 through a forward scatter angle of about 40° to produce scatter signal VS.

Referring to FIGS. 3 and 4, one of the functions of nozzle 21 is to deloop entities 31, such as fibers. FIG. 3 shows a front view and FIG. 4 shows a back view of the nozzle 21. The front view as shown in FIG. 3 faces the light beam 29 as shown in FIG. 1. The nozzle 21 includes an inlet section 60, coupled to center section 62, which in turn, is coupled to an outlet section 64. The inlet section 60 includes a cylindrical inlet bore 66 leading to a tapered cylindrical passageway 68 which extends continuously through the inlet section 60 and the middle section 62 to an optical aperture 70 which includes an entrance aperture 71, an exit aperture 72 and a tapered passageway therebetween. A slightly tapered passageway 74 extends from the optical aperture 70 through the middle section 62 and outlet section 64 of the nozzle 21 to a cylindrical outlet bore 76. The inlet and outlet bores are for coupling to ½" inside diameter pipe such that the transition from the inside diameter of the pipe to the inside diameter of the tapered sections will be smooth.

Figure 5:
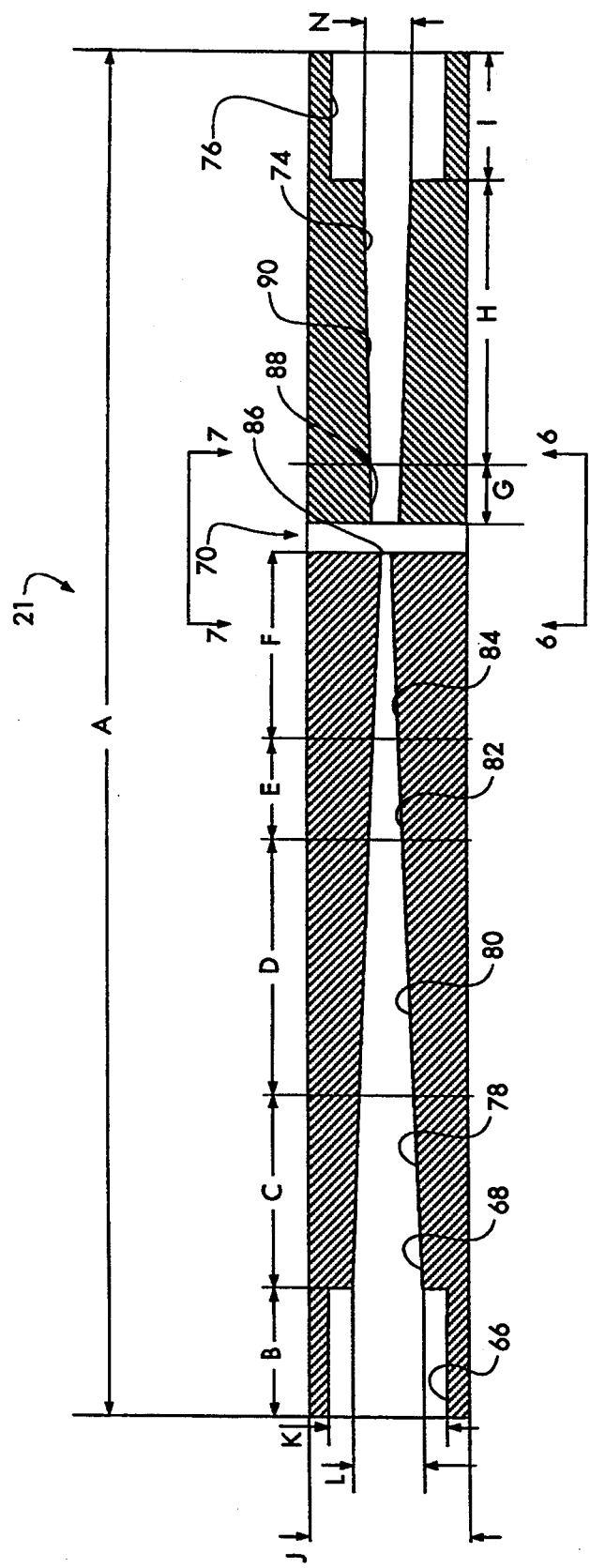
FIG. 5 is a cross-sectional view of the nozzle viewed in accordance with section lines 5—5 in FIG. 3.

Referring now to FIG. 5, there is shown a more detailed section view of the nozzle 21 taken through section lines 5—5 shown in FIG. 3. In this views it will be appreciated that the three sections of the nozzle 21 function to create a continuous nozzle 21 having a length A of 8.775 inches. The illustration of FIG. 5 omits designations of the three sections 60, 62, and 64, for clarity of illustration, it being understood that the nozzle need not be physically divided into separate sections.

As best shown in FIG. 5, the inlet bore 66 has a length B of 0.250 inch and the tapered passageway 68 extends therefrom and consists of four end-to-end tapered sections, 78, 80, 82, and 84, in that order. Section 78 extends from the end of bore 66 inwardly for a distance C of 1.500 inches. Section 80 extends from section 78 into the nozzle for a distance D of about 2.215 inches. Section 82 extends from the end of section 80 into the nozzle for a distance E of about 0.750 inch, and section 84 extends from section 82 for a distance F of 1.535 inches terminating at the nozzle minimum cross-section 86, where its minimum diameter is 0.110 inch. Thus, the tapered sections C, D, E, and F have a total length of 6.000 inches.

Figure 6:
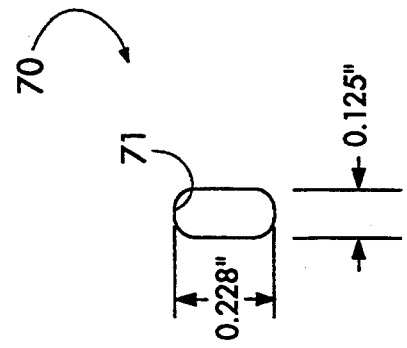

The half-angle or taper per side of section 78 is 5°, of section 80 is 3°, of section 82 is 1.18°, and of section 84 is 1.12°. The outside diameter of the nozzle 21, in this preferred embodiment is J, 0.750 inch. The diameter of the inlet bore 66 is K, 0.625 inch, and the largest diameter of the tapered section 68 is L, 0.500 inch. The smallest diameter of section 84 is 0.110 inch. The distance across the optical aperture 70 as shown in FIG. 6 is 0.125 inch.

The tapered passageway 74 is divided into two sections: section 88 having a length G of 0.300 inch and no taper (i.e., straight section) and has a diameter of 0.216 inch, and section 90 having a length H of 1.850 inches and a taper of 3°. Section 90 tapers from 0.216 inches to 0.305 inches at the point where section 74 terminates at outlet bore 76. The outlet bore 76 has a length I of 0.250 inch and a diameter K of 0.625 inches.

Still referring to FIG. 5, it should be appreciated that the tapered section 68 of the inlet nozzle 21 is longer and has a more gradual taper than nozzles that have conventionally been used in AFIS instruments. An early AFIS nozzle (referred to as AFIS0 nozzle) had a tapered inlet or accelerating section having a length of 2.891 inches with a three degree taper terminating at an outlet opening having a diameter of 0.188 inch. A later AFIS nozzle (referred to as AFIS1 nozzle), prior to the present invention had a tapered front accelerating section having a length of 2.800 inches with an entrance taper of 5° for 1.050 inch, a second taper of 3° for 0.750 inch, a third taper of 1.6° for 0.500 inch and a final taper of 0.8° for 0.500 inch terminating at an outlet aperture having a diameter of 0.191". An experimental nozzle (referred to as 15° nozzle) built in accordance with the aforementioned paper had a length of 0.799 inch with a taper of 15° terminating at a circular aperture having a diameter of 0.110 inch. (It should be noted that the paper did not actually concern AFIS type nozzles, so the experimental nozzle represents the inventors' attempted adaptation of the paper's teaching to AFIS type nozzles.) The paper suggested improved delooping characteristics could be achieved by modifying the conventional AFIS nozzle so that its taper was greater, which would increase the acceleration per unit length and was believed to improve the delooping characteristics of the nozzle. Their objective was to present unlooped fibers for rotor spinning, not for measurement. To achieve this increase in taper, the taper length would have to be decreased. However, it has been discovered that precisely the opposite is true. To increase the delooping characteristic of a nozzle in an AFIS type environment, it was discovered that the length of the nozzle should be increased and the overall taper decreased. The nozzle depicted in FIG. 5 represents the best nozzle currently known to the applicants and it produces the delooping characteristics shown in Table 1 below comparing nozzle 21 (QT3A-1 in the table) to conventional AFIS nozzles (AFIS0 and AFIS1 in the table) and an experimental nozzle built in accordance with the teachings of the paper which is designated as the Fifteen Degree (15°) nozzle in the table. AFIS0 and AFIS1 nozzles are 2 piece nozzles and QT3A-1 and the Fifteen Degree (15°) nozzle are 1 piece nozzles. A one piece nozzle has the advantage of mechanical rigidity and ease of alignment.

Table 1 represents the delooping characteristics of each of the nozzles when the fibers are each presented to the nozzle 21 in a 100% looped condition and a 100% straight condition. Of course, both of these conditions would not represent a normal operating condition in an AFIS device since the fibers would be naturally presented to the nozzle in a variety of conditions, such as looped, partially looped and straight. However, the experimental data shown in the above chart shows the dramatic improvement in delooping characteristics achieved by the nozzle 21 of the present invention.

In Table 1, the first column labelled "NOZZLE ID" identifies four nozzles that were tested, and the information in each row was obtained for the nozzle identified in column 1. The second column shows the drop condition for each of 50 fibers that were dropped into each nozzle, and the condition is either straight or looped. Column 3 shows the air flow rate through the sensor in cubic feet per minute and column 4 shows the gas velocity in meters per second as the gas is exiting the accelerating section of the nozzle. The velocities of column 4 are calculated rather than measured velocities.

nozzle straight and all 100% looped fibers went through the nozzle 100% looped then the ratio of this column would be 50% which means that the 100% looped fibers have a length of 50% of the straight fibers. Thus, it will be appreciated that the delooping effect of QT3A-1 (86−50%=36%) may be regarded as almost twice that of the other nozzles (66%−50%=16%;

TABLE 1

HAND DROP FOR 1.5 INCH × 1.5 DENIER POLYESTER

| 1 NOZZLE ID | 2 DROP CONDITION | 3 SENSOR FLOW Q (cfm) | 4 GAS VELOCITY Vg (CALC) | 5 FIBER ENTRANCE VEL (Vb) m/s | 6 FIBER EXIT VEL (Vf) m/s | 7 AVG FIBER VEL (Vf) m/s | 8 MEAN LENGTH OF DIST. (mm) | 9 NORMALIZED MEAN LENGTH OF DIST. | 10 RATIO OF MEAN LENGTH LOOP/STR |
|---|---|---|---|---|---|---|---|---|---|
| QT3A-1 | STRAIGHT | 1.3 | 100 m/s | 61 | 70 | 67 | 41.2 | 38.1 | |
| | LOOPED | | | 62 | 68 | | 35.6 | 33.0 | 86% |
| AFIS1 | STRAIGHT | 3.9 | 100 m/s | 43 | 72 | 58 | 38.9 | 38.1 | |
| | LOOPED | | | 52 | 65 | | 25.7 | 25.2 | 66% |
| AFIS0 | STRAIGHT | 3.9 | 100 m/s | 36 | 67 | 47 | 41.1 | 38.1 | |
| | LOOPED | | | 41 | 58 | | 24.4 | 22.6 | 59% |
| 15 DEGREE | STRAIGHT | 1.3 | 100 m/s | 13 | 47 | 24 | 35.8 | 38.1 | |
| | LOOPED | | | 13 | 45 | | 25.4 | 27.0 | 70% |

Columns 5 and 6 of Table 1 show the average fiber velocity for the 50 fibers as they exit the accelerating portion of the nozzle. Column 5 shows the velocity of the leading end of the fiber as it enters the test zone and column 6 shows the velocity of the trailing end of the fiber as it exits the test zone. Column 7 shows the average velocity of the 50 straight dropped fibers for each of the nozzles. The average fiber velocity was obtained by measuring the average fiber velocity for each of the 50 straight dropped fibers, and then averaging those 50 measurements. The measured average fiber velocity for each fiber was obtained by determining the time required for the fiber to pass by a sensor and then dividing the length of the fiber (38.1 mm) by the measured time. Column 8 shows the mean measured length of the 50 fibers, and column 9 shows a normalized mean measured length for the 50 fibers. Column 9 is obtained from column 8 by multiplying the numbers of column 8 by a correction factor, which is 38.1 divided by the mean measured length of the straight dropped fibers. For example, the correction factor for the nozzle "QT3A-1" is 38.1/41.1. Likewise, the correction factor for the "AFIS1" nozzle is 38.1/38.9. Finally, column 10 shows the ratio of mean length of the loop dropped fibers to the straight dropped fibers. For example, for QT3A-1, the mean length of the loop dropped fibers was 35.6 and for the straight dropped fibers was 41.1. Thus, the ratio shown in column 10 is 35.6 divided 41.1, which equals 86%.

Referring to Table 1, it is first noted that the nozzles are all operated at 100 m/sec gas velocity at the nozzle exit as indicated by column 4, and this velocity is not necessarily the ideal operating condition for all of the nozzles, but it is near the optimum and provides an unbiased condition for comparison purposes. Referring to column 8 entitled "Mean Length of Distribution," it is noted that the straight dropped fibers have varying length measurements when measured on the varying nozzles. This variation is caused by variation from nozzle to nozzle in the speed of the fiber and forces on the fiber as it exits the nozzle and is normally corrected by calibration. However, this calibration does not affect the numbers in the last column which shows the ratio of the mean measured length of straight dropped fibers to the mean measured length of 100% looped dropped fibers. If all straight dropped fibers went through the 59%−50%=9%; and 70%−50%=20%), and when conditions for all nozzles are idealized, an even greater delooping advantage is achieved by the nozzle of the present invention.

The data shown in Table 1 are also shown graphically in FIGS. 16-19 and the delooping superiority of the nozzle 21 (QT3A-1) is clear. FIG. 16A shows the means and distribution for the length of 50 fibers hand dropped straight into the nozzle inlet. Each fiber measured was verified to be straight by observation of the electrical waveform on a digitizing oscilloscope. The fact that there is a distribution for these measured lengths is due to noise or uncertainties in the measurement system. As such, if a length measurement of a fiber dropped 100% looped falls within this distribution (mean±2 std.dev.), we will define it as straight. For present purposes, a fiber is considered delooped when its measured length is within two standard deviations of the mean measured length of N fibers dropped into the nozzle in a straight condition, where N is preferably 50 but may vary depending on the fiber type and length and operating condition. FIGS. 16A and 16B show the measured length of straight dropped fibers and 100% looped dropped fibers, respectively, when using nozzle 21 (QT3A-1). The mean measured length of straight dropped fibers was 41.2 mm and the standard deviation was 3.2. Thus, a delooped fiber has a measured length of between 34.8 mm and 47.6, and a large majority of the fibers represented in FIG. 16B are delooped as indicated by bracket 200.

FIGS. 17A and 17B show the measured length of straight dropped fibers and 100% looped dropped fibers, respectively, when using an AFIS1 nozzle. As indicated by bracket 202, few of the 100% looped dropped fibers were delooped, i.e. were measured as having a length between 34.9 and 42.9, where the mean measured length of straight dropped fibers was 38.9 and a standard deviation was 2.0. Likewise, referring to FIGS. 18A and 18B, the AFIS0 nozzle produced few delooped fibers, which are indicated by bracket 204, and referring to FIGS. 19A and 19B, the Fifteen Degree (15°) nozzle produced more delooped fibers, which are indicated by bracket 206, than AFIS0 or AFIS1 nozzles, but the number of delooped fibers for the Fifteen Degree (15°) nozzle was still substantially less than the number produced by nozzle 21. Moreover, a visual comparison of FIGS. 16A and 16B to FIGS. 19A and 19B reveals that the nozzle 21 produces a measured length distribution that is similar for both looped and straight dropped fibers, whereas the fifteen degree (15°) nozzle does not. This fact further illustrates that the nozzle 21 is achieving superior delooping.

While nozzle 21 represents the best known nozzle for delooping 1.5 denier polyester fibers having a length of 1.5 inches carried in an optimized airflow of 1.3 CFM, it will be understood that the length, taper magnitude and taper geometry of nozzle 21 and the optimum flow rate would vary with particular applications and conditions. However, based on our experimental data, nozzles having a length greater than three (3) inches and a taper of less than three degrees (3°) should have improved delooping characteristics as compared to conventional AFIS nozzles.

Figure 8:
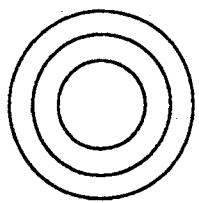
FIG. 8 is a view of the nozzle taken along view lines 8—8 shown in FIG. 3.
Figure 7:
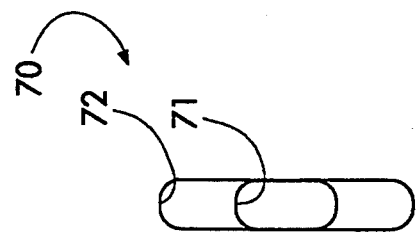
FIGS. 6 and 7 are front and rear views of an optical window when viewed as indicated by lines 6—6 and lines 7—7 shown in FIG. 5.

FIGS. 6, 7, and 8 are sectional views corresponding to section lines 6—6 and 7—7 shown in FIG. 5 and section lines 8—8 shown in FIG. 3. FIG. 7 shows a back view of the optical aperture 70 and FIG. 6 shows a front view of the aperture 70. FIG. 8 shows the end view of the outlet section 64 of nozzle 21.

Electronic Delooping

Even though nozzle 21 offers considerably improved delooping characteristics, further improvement in data acquisition may be achieved by electronically delooping the fibers 31. In the present invention, the computer 114, which preferably includes digital signal processing circuitry (DSP), electronically deloops the waveform produced by a looped fiber and then determines characteristics of the fiber, such as the length of the fiber, by the method described below.

Figure 9:
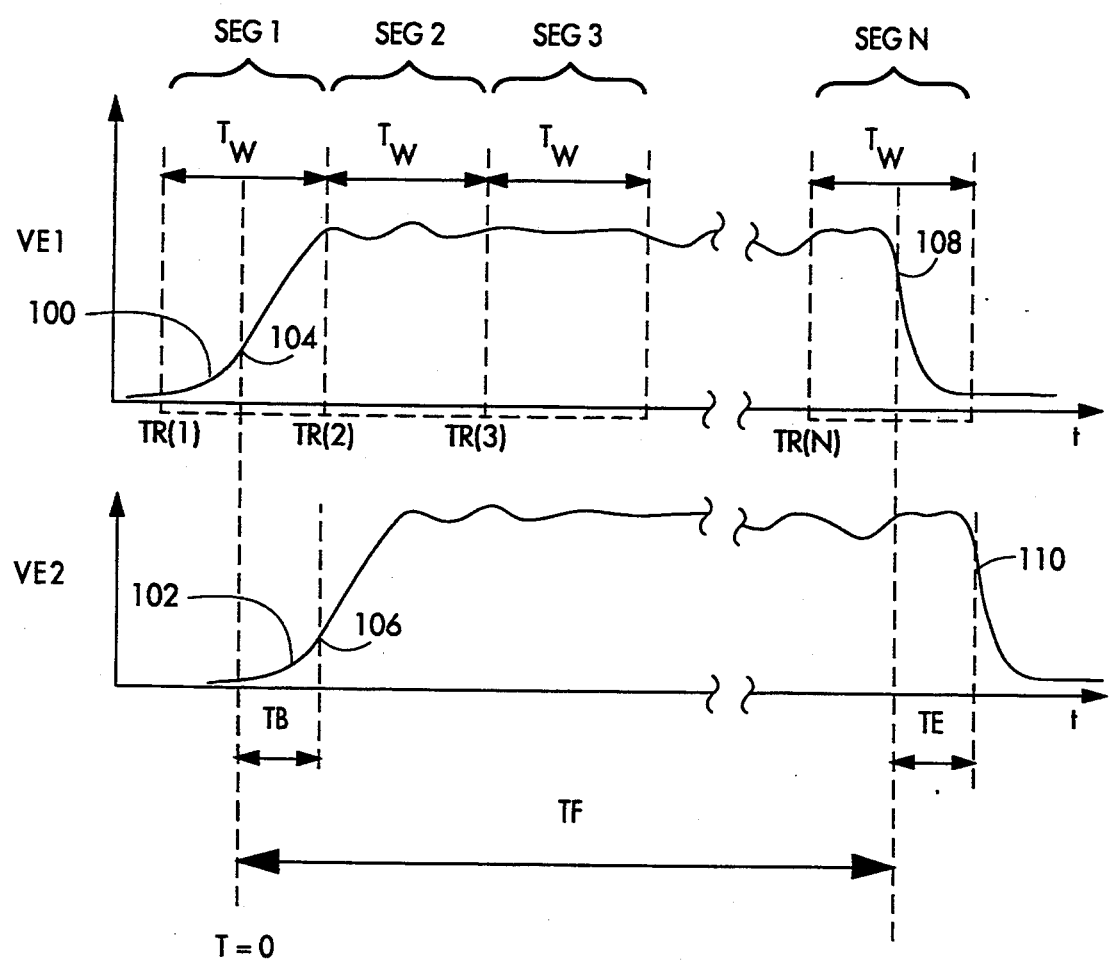
FIG. 9 is a graphical representation of two electrical voltage signals, VE1 and VE2, produced by the two photodetectors and graphed against time on the horizontal scale.

Referring again to FIG. 1, it will be appreciated that as an entity 31 (fiber 31) travels in front of extinction detectors 25A and 25B, signals will be respectively produced which are designated as VE1 and VE2 in FIG. 1. The waveforms of VE1 and VE2 are graphically depicted in FIG. 9 as waveforms 100 and 102, respectively. In FIG. 9, the vertical axis of the waveforms 100 and 102 represents voltage and the horizontal axis represents time. Because sensors 25A and 25B are sensing extinction of light, it will be understood that VE1 and VE2 are actually measures of the decrease in amount of light received by sensors 25A and 25B.

Referring to FIG. 9, the waveform 102 is lagging behind the waveform 100 in time, but is otherwise almost identical to the waveform 100. Considering the positions of the sensors of 25A and 25B shown in FIG. 1, this time lag is to be expected. The presence of a fiber or an entity is detected by computer 114 at point 104 on waveform 100 and is detected at point 106 on waveform 102. It will be noted that these points 104 and 106 are corresponding points on the two waveforms. These points may be determined by referencing the two waveforms 100 and 102 to a threshold voltage (which is done in conventional AFIS devices), or by other techniques such as monitoring the slope of the two waveforms and selecting points 104 and 106 based on the waveform slope exceeding a predetermined magnitude. Likewise the end of the waveforms 100 and 102 are detected at points 108 and 110. Again, the end of the waveform may be detected by observing when the waveform drops below a threshold voltage or by other appropriate means such as observing the slope of the waveform.

Once the waveform is detected, the preferred method of determining the correct length of a looped accelerating fiber 31 is done in two steps. First, the computer 114 compensates for the acceleration of fiber 31 to produce a compensated waveform with uniform velocity (no acceleration). Second, it deloops the compensated waveform to determine the actual length of the unlooped fiber 31. Preferably, this processing is achieved by digital signal processing using DSP chips separate from the control processor of computer 114.

Compensation for fiber acceleration is accomplished by first breaking the waveform 100 into N equal time segments, where N equals the total number of segments with each segment having the same number of samples or data points. (See FIG. 9.) In the preferred embodiment the waveforms VE1 and VE2 are sampled by an A/D converter 112 and are input as samples into a computer 114. Since the sampling is done at uniform time intervals, the number of samples is directly proportional to the time duration of the waveform. Thus, time is regarded as equivalent to the number of samples. In the preferred embodiment, an IBM compatible PC computer is programmed to perform the delooping method described herein, but it will be understood that other computing hardware could be used or the method could be performed by hand.

Next, one determines the delay time from waveform 100 (VE1) to waveform 102 (VE2) for each segment. If this delay time is divided into the effective edge-to-edge detector spacing (preferably about one millimeter) between sensors 25A and 25B, then the velocity VEL(n), for each segment is obtained where n is the segment number. Segments where the fiber 31 is traveling slower represent a smaller section of the actual fiber 31 than segments where the fiber 31 is traveling faster. The acceleration correction consists of scaling the time of each segment by reducing the number of data points or samples in the slower segments based on the speeds of the slower segments compared to the speed of the fastest segment. In other words, the number of samples in a particular slow segment will be reduced by a ratio equal to the slow segment's speed divided by the fastest segment's speed. After such reduction, the time of each segment will be proportional to the actual fiber section length for the segment at a velocity equal to the fastest (last) segment. The corrected fiber time, TFC, will be proportional to the actual length of the fiber traveling at the highest velocity over its entire length.

After the acceleration compensated fiber waveform is obtained, delooping is accomplished in one embodiment by identifying the average diameter for a non-looped section and dividing the total area of the acceleration compensated waveform by the average diameter of the non-looped section. The result is an unlooped compensated fiber time, TFCU, proportional to the length of the unlooped fiber traveling at the velocity of the fastest (last) segment. Length is determined by multiplying the unlooped compensated fiber, TFCU, by the velocity of the fastest (last) segment of the fiber waveform.

One form of the above described method may be best understood by reference to FIGS. 9-14, beginning with FIG. 9 which illustrates two extinction waveforms from the sensors 25A and 25B. VE2 is delayed in time from VE1 proportional to the effective spacing (about one millimeter) between the sensors 25A and 25B and inversely proportional to the speed of the fiber 31. The waveform 100 (VE1) is divided in N segments, as shown, with widths TW.

Figure 12:
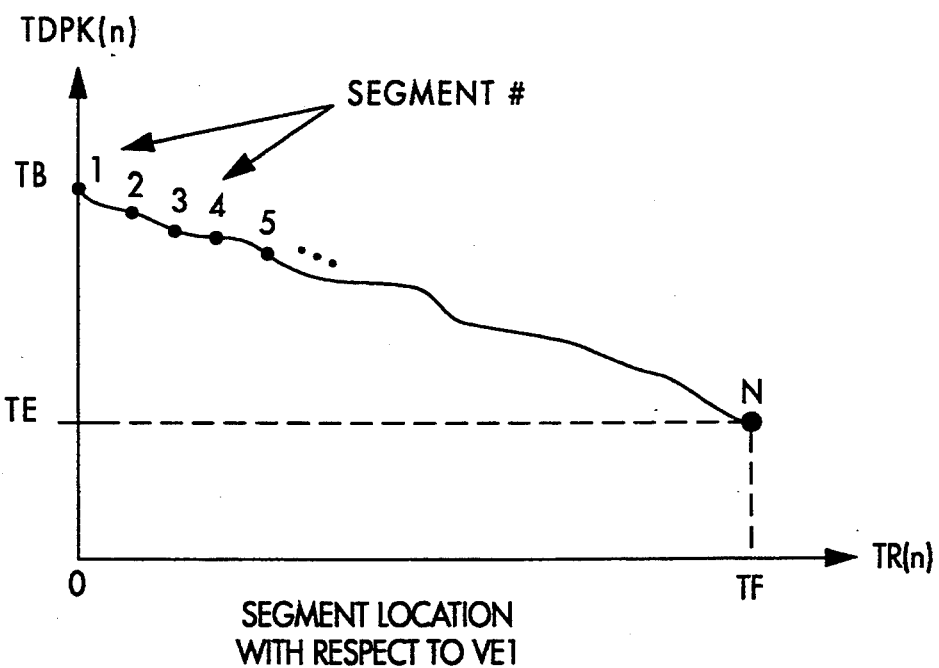
FIG. 12 is a graph of the velocity represented by each segment of VE1, which is represented in the vertical dimension against time location of the segment which is represented in the horizontal dimension.

FIG. 10 shows a plot of each segment of VE1 and its corresponding cross-correlation to waveform VE2. Notice how the peak in the cross-correlation shifts from a time delay between VE1 and VE2 of TB for the first segment to a value of TE for the Nth (last) segment, where TB is the time delay between the waveforms 100 and 102 at the beginning of the fiber 31 (leading end) and TE is the time delay at the end of the fiber 31 (trailing end). TB is greater than TE due to the fact that when the fiber 31 enters the sensing volume 116 (FIG. 1) it is traveling slower than when it exits, by design. If one plots the delay time of the peak for each segment, TDPK(n), versus the location of the segment relative to the fiber time, TR(n), then a plot is obtained indicating how the fiber accelerates from the time it enters the sensing volume until it exits (FIG. 12).

Figure 11:
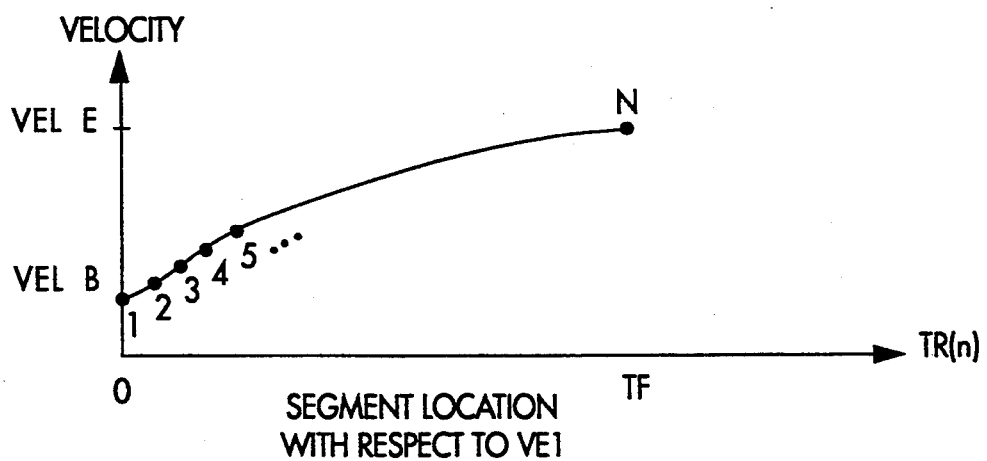
FIG. 11 is a graph of the time delay for the peak of the cross-correlation for each of the segments of VE1 cross-correlated against VE2 with time location of the segment being represented in the horizontal dimension and time delay for the peak being represented in the vertical dimension.
Figure 13:
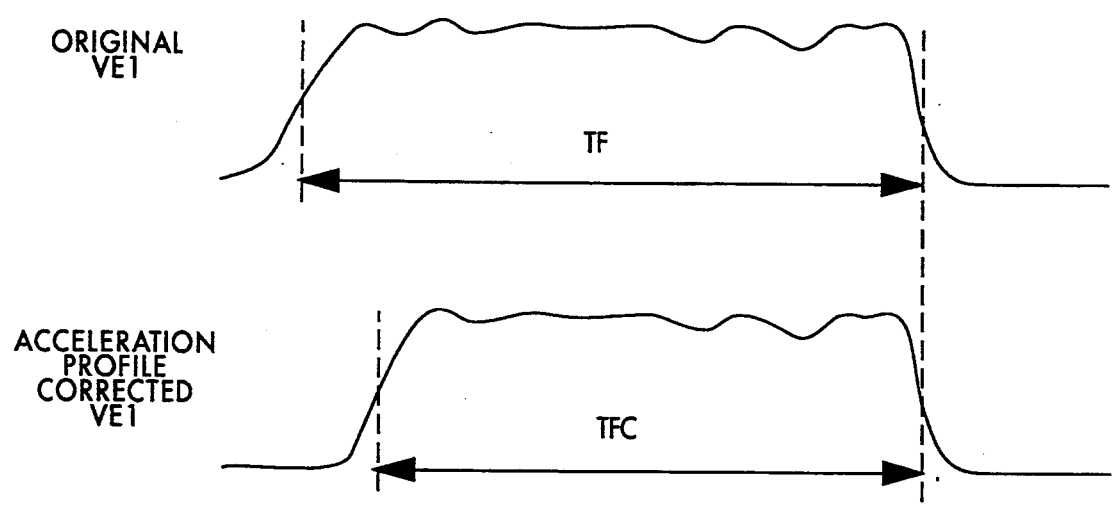
FIG. 13 is a graphical comparison of the original VE1 signal as compared to the acceleration corrected VE1 signal.

The velocity for each segment is obtained by dividing the effective spacing between sensors 25A and 25B by the delay time for that segment. Plotting the segment velocities versus the location of the segment relative to the fiber time produces the velocity profile for the entire fiber which is shown in FIG. 11. Velocity correction is obtained by reducing the number of data points in each segment, n, by the factor TDPK(N)/TDPK(n) where TDPK(N) is the delay time for the fastest (last) segment and TDPK(n) is the delay time of the nth segment, for all the segments preceding the last segment, N. (TDPK(N)/TDPK(n) equals VEL(n)/VEL(N) where VEL(n) is the velocity of the nth fiber segment and VEL(N) is the velocity of the Nth segment, the last and fastest segment.) Recall that the number of data points in each segment is a measure of time and may be thought of as equivalent to time. The data points removed should be equally spaced through the segment. The resultant array is a description of the fiber waveform VE1 traveling at a constant velocity equal to the velocity of segment N which is graphically shown in FIG. 13.

More needs to be said about the two limiting cases of this method. If the number of segments is equal to 2, this method is approximately the same as determining the delay between the rising edges of the two original waveform (TB) and the falling edges of the two waveform (TE). In this case, no additional information about the velocity profile is known but solid values for TB and TE are obtained. As the number of segments increases, the number of distinguishing features on the waveforms which produce a peak in the cross-correlation are reduced. As such, the peak in the cross-correlation for the inner segments will diminish and become less discernable. This results in a velocity profile curve with a significant amount of noise between the first segment (TB) and the last segment (TE). The method described herein involves looking at the CV (standard deviation expressed as a percentage of the measured event) of the noise in the velocity profile to determine the optimum number of segments. When the CV due to the noise exceeds a selected limit, preferably 25%, then the algorithm must use the previous determination of the velocity profile.

Figure 14B:
FIG. 14B is a graphical representation of the looped fiber which produced the waveform in FIG. 14A.
Figure 14A:
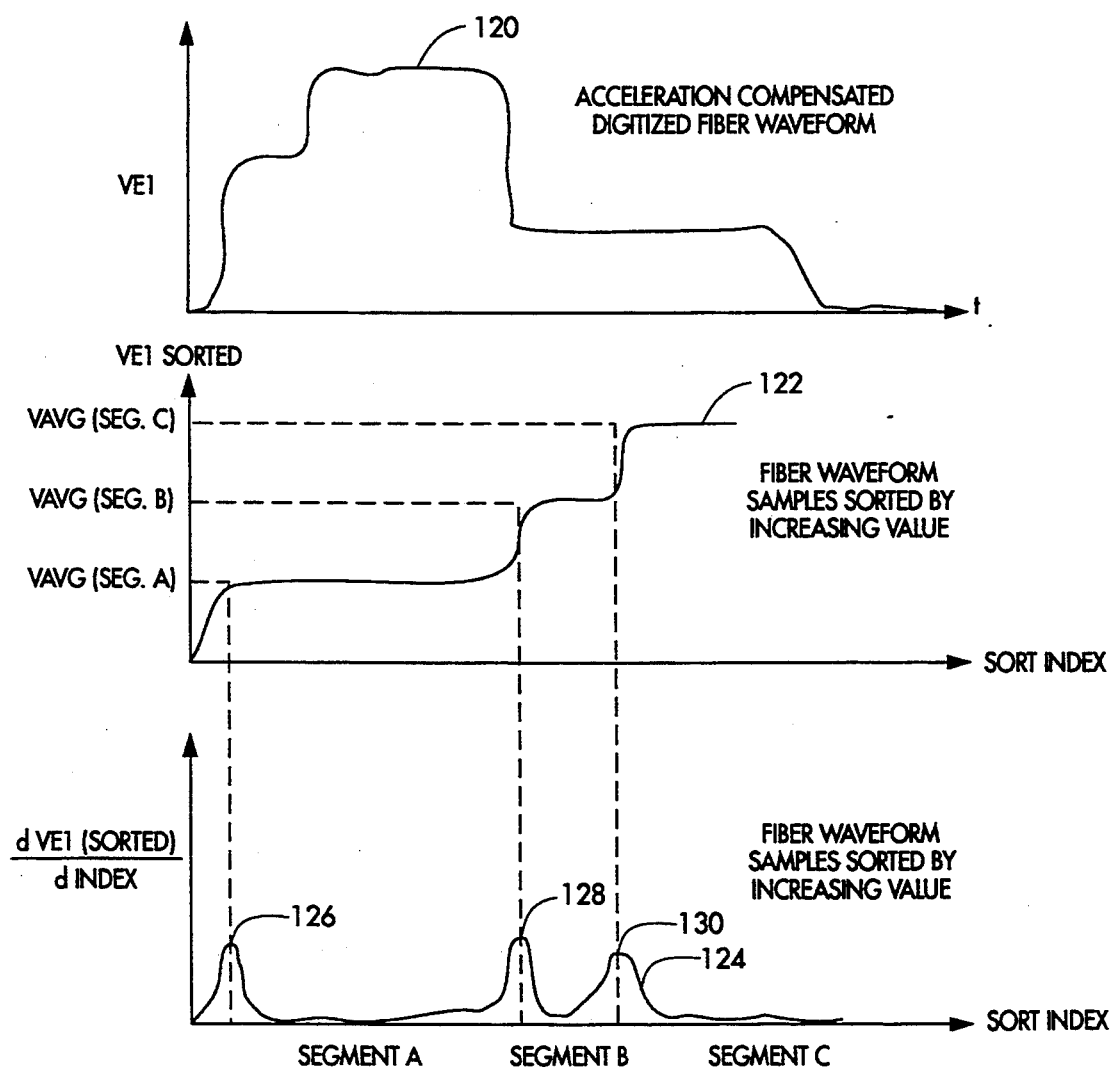
FIG. 14A is a graphical representation of a hypothetical detector signal VE1 (top graph) compared to sorted waveform (middle graph) which represents VE1 samples sorted according to magnitude of the signal, and further compared to a derivative waveform (bottom graph) which represents the first derivative of VE1 sorted (the middle graph)

FIG. 14A graphically represents an acceleration compensated waveform 120 (VE1) produced by a fiber 121 that is looped with double and triple diameter sections as shown in FIG. 14B. Fiber delooping can be accomplished several ways. The preferred method begins by sorting the acceleration compensated fiber waveform 120 of VE1 samples by increasing values as shown in FIG. 14A to produce a sorted waveform 122. By taking the simple two-point derivative of the sorted results with respect to the sort index, one can locate the unlooped diameter of the fiber 121. In FIG. 14A, waveform 124 is the derivative of sorted waveform 122, and it has three peaks 126, 128 and 130, which mark the beginnings of three segments A, B and C, respectively, of sorted waveform 122. The peaks are found by determining the largest value in the waveform 124, setting a threshold equal to a fraction of the largest value (preferably 0.60) and locating segments of waveform 124 that exceed the threshold. The vertical height of segment A of waveform 122 represents the diameter of an unlooped fiber. As shown in FIG. 14A, this diameter is denoted by VAVG(SEG.A). The diameter of this unlooped section is determined by taking the average of the sample values of waveform 122 between the first (126) and second (128) peak of the derivative waveform 124. The acceleration compensated fiber time for fiber 121 in an unlooped condition (TFCU) can then be determined by dividing the area under the waveform by the diameter (VAVG[SEG.A]) of the unlooped section. The fiber length is then determined by multiplying speed of the fastest (last) segment of fiber 121, as determined above, by this corrected fiber time, TFCU. In addition, the number of peaks after the first peak in the derivative waveform 124 are indicative of the number of loops in the fiber. The integrity of a loop is qualified by evaluating the average of the values for the looped section(s) to see if they are approximately 2X, 3X, ... the diameter of the unlooped section for double loops, triple loops, etc.

Another method for determining the TFCU of an unlooped fiber is by adding the time (number of samples) between the first two peaks of the derivative, plus twice the time between the second and third peak (Segment B), plus three times the time between the third and fourth peak (Segment C), etc. The fiber length is then determined as described above using this value for TFCU.

Figure 15A:
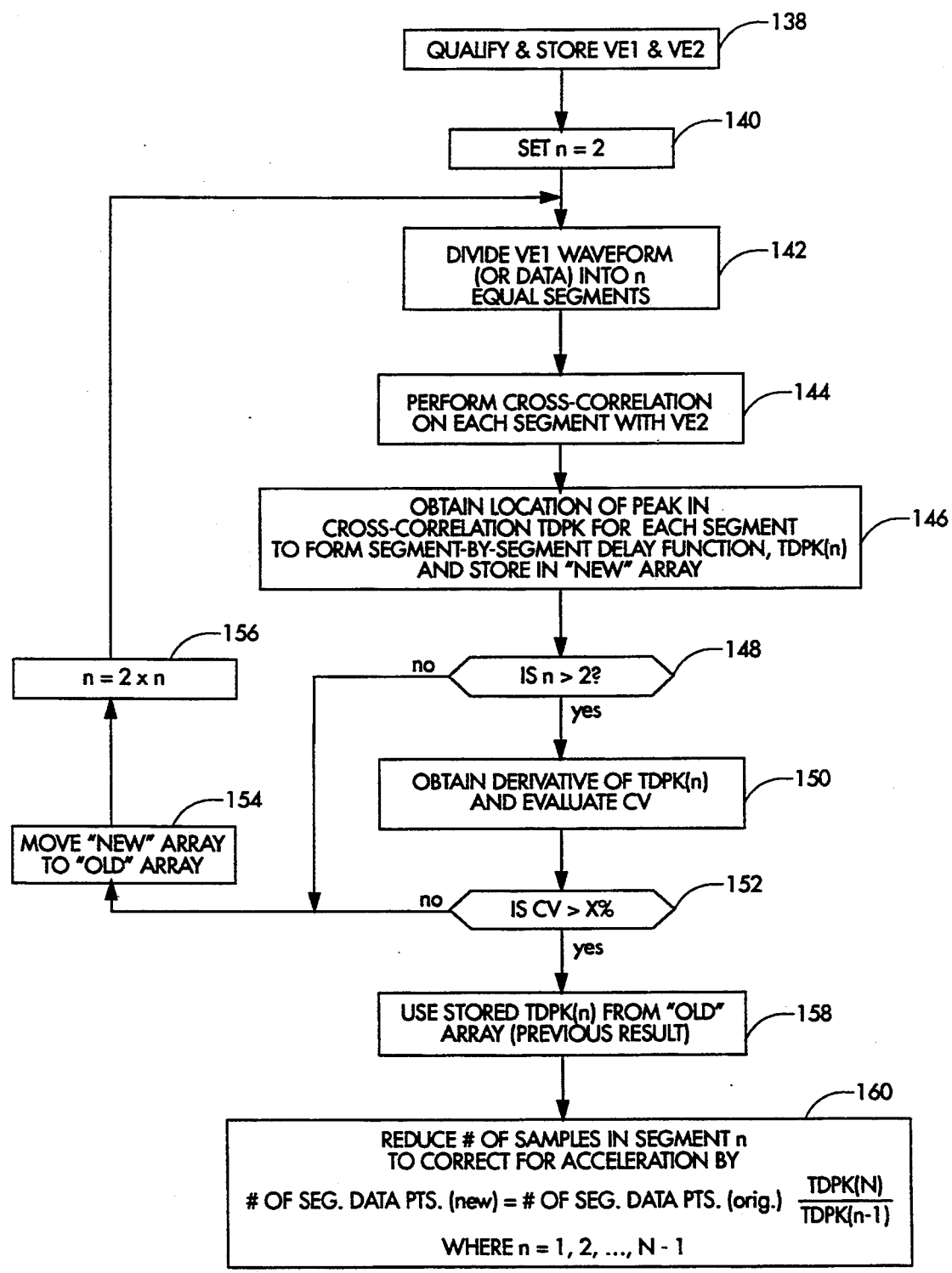
FIGS. 15A and 15B represent a flow chart illustrating one embodiment of a program used in the present invention.
Figure 15B:
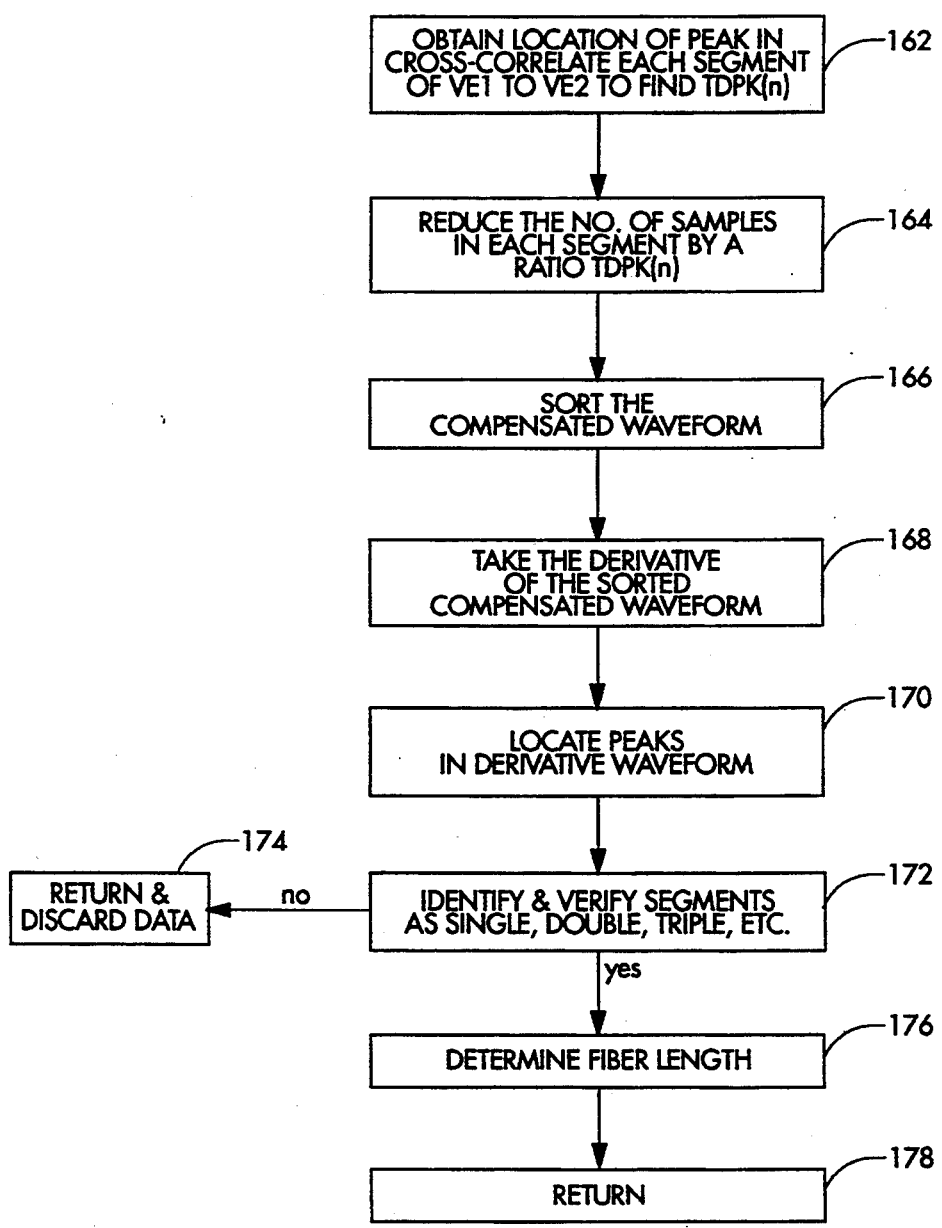

FIGS. 15A and 15B represent a flow chart for a portion of the above described program providing additional detail as to how the number (N) of segments is determined.

To begin at step 138, the uniform time interval samples of the two waveforms VE1 and VE2 are first identified as representing a fiber and stored in two different arrays, VE1 and VE2. A waveform is identified as a fiber, generally, if its aspect ratio (length/diameter) is greater than about three to about ten in this case, if the waveform's time (TF) divided by its average amplitude is greater than 1.6 microseconds/volt. The process of identifying fibers is described in more detail in co-pending application Ser. No. 07/962,898, entitled APPARATUS AND METHOD FOR TESTING MULTIPLE CHARACTERISTICS OF SINGLE TEXTILE SAMPLE WITH AUTOMATIC FEED. Next, at step 140 a variable n is set equal to 2. Then, at step 142 the array for VE1 is divided into n equal segments. A cross-correlation is performed with each of the VE1 segments and the entire VE2 array at step 144. The location of the peak in the cross-correlation of each segment of VE1 is obtained and stored in NEW array at step 146. This array is the segment-by-segment delay function, TDPK(n). At step 148 the variable n is compared to 2. If n is greater than 2, the program proceeds to step 150. If n is less than or equal to 2, it goes to step 154. On the first pass through, the program will go to 154 since n=2. At step 154, the array NEW is moved to an array OLD for temporary storage. At step 156, n is doubled and the program begins again at step 142. If n was greater than 2 at step 148, then the derivative of the delay function TDPK(n) in array NEW is determined as step 150. The standard deviation and Coefficient of Variation (CV=100 X std.dev./mean) of the derivative values is also determined. This CV is used to determine the quality of the delay function obtained in step 146. In step 152, the CV is compared to a predetermined limit X. In the preferred embodiment, X is 25%. If the CV is less than or equal to X, then the program goes to step 154, the "NEW" array is stored as the "OLD" array and the program repeats step 156 and returns to step 142. If the CV is greater than X, then the program goes to step 158. Here, the results (array "OLD") of the previous determination of the delay function which produced a derivative CV less than X is retrieved. At step 160 the number of samples in each segment of VE1 are reduced proportional to the velocity of that segment relative to the velocity of the fastest (last) segment of VE1, as previously described.

A few additional comments will further help to better understand the portion of the computer program flowchart described above. The objective of the program is to compensate for the acceleration of the fiber to produce an equivalent fiber waveform if the fiber were traveling at a constant velocity equal to the fastest segment. It begins by dividing the waveform into only two segments. These two segments will produce an excellent cross-correlation since there will be many features in each segment which will correlate well with the corresponding features in VE2. However, the ability to compensate the VE1 waveform for acceleration is limited since only two data points are available for defining the acceleration or velocity profile. It is therefore desirable to increase the number of segments used as much as possible. As the number of segments is increased, the number of features present in each segment will decrease, and, therefore, the peak in the cross-correlation which identifies the delay between the VE1 segment and VE2 will decrease. The method for detecting the maximum useable number of segments looks at the "noise" in the time delay function. This is done by taking the derivative of the time delay function and evaluating the CV of this derivative. When the CV exceeds the desired limit X, the program has exceeded the useable number of segments. It then reverts back to the previous determination and uses those results. The value used for X can vary depending upon the application. Cotton will have many distinguishing features along its length, whereas uncrimped polyester or rayon will have very few distinguishing features. Thus, shorter segments may be used for cotton fibers as compared to uncrimped polyester or nylon. In addition, the needs of the customer will affect the value of X. A small value for X will produce a more accurate determination of fiber length, but the time required to complete the required computations will be longer.

The remaining portion of the flow chart shown in FIG. 15B follows directly from the description of the method set forth above. As indicated at step 162, each segment of VE1 is cross-correlated to VE2 to find the peak correlation delay time, TDPK(n), and as indicated at step 164, the number of samples in each segment is reduced by a ratio of TDPK(N) 30 TDPK(n), which produces an acceleration compensated waveform shown in FIG. 14A. At step 166, the compensated waveform is sorted according to the voltage magnitude of each sample to produce a sorted compensated waveform which is shown as the middle graph in FIG. 14A. As indicated at step 168, a derivative waveform is produced by taking the derivative of the sorted compensated waveform, and the major peaks of the derivative waveform 124 are located and correlated back to the sorted compensated waveform. As indicated at step 172, segments of the waveform 122 are located based on where the peaks 126, 128 and 130 occurred in the derivative waveform 124. To verify that the various segments correspond to single fiber segments, doubled fiber segments, tripled fiber segments, etc., the magnitude of segment A is divided into the magnitudes of segments B, C, etc., and the quotient should be within $+/-0.5$ of 2 for segment B, 3 for segment C, etc. If the fiber segments do not meet this criteria, the program proceeds to block 174, discards the data and returns to begin the program again with new data.

If the criteria of single, double, triple, etc., fibers is met, the program proceeds to block 176 where it determines the fiber length in one of the two methods previously described. Then, as indicated by step 178, the program returns to the beginning to start again with new data.

From the above description, it will be appreciated that the present invention provides an efficient apparatus and method for "delooping" individual fiber measurements. although preferred embodiments have been described as examples, it will be understood that the present invention is capable of numerous, rearrangements, modifications and substitutions without departing from the scope of the invention. In the case of physical delooping, the fiber is acted upon to physically remove looped conditions, whereas electronic delooping is accomplished by manipulating the data of a looped fiber to accurately determined fiber characteristics from the data with appropriate compensation for acceleration and the looped condition of the fiber.

What is claimed is:

1. An apparatus for sensing characteristics of entities carried in an air flow, at least a portion of the entities being in an undesired physical condition, comprising:
a sensing volume;
entity presentation means including at least a tapered accelerating passageway having a length greater than about 3 inches and a taper of less than about 3° for receiving the entities from the air flow and accelerating the entities in the tapered accelerating passageway, presenting a first portion of the entities to said sensing volume in a desired physical condition and presenting a second portion of entities in an undesired physical condition, said entity presentation means operating on said entities to increase the proportion of entities in a desired physical condition in said sensing volume as compared to the entities in the air flow;
sensor means for sensing the entities in said sensing volume and producing a sensor signal corresponding to characteristics of the sensed entities; and
analyzing means for receiving and analyzing said sensor signal to produce output representing characteristics of the sensed entities.

2. The apparatus of claim 1 wherein said apparatus further comprises:

separation means for receiving the entities and air flow and for separating entities from at least a portion of the airflow;

a first output for outputting at least a portion of the airflow substantially without the entities; and a second output for outputting a second airflow with the entities carried therein, wherein the second output is connected to the entity presentation means.

3. The apparatus of claim 2 wherein said apparatus further comprises:

a conditioned input for inputting a predetermined flow of conditioned gas into said separation means so that a desired proportion of the second airflow is constituted by the conditioned gas.

4. The apparatus of claim 1 wherein said apparatus further comprises:

a cyclone separation chamber;

a first input found in said cyclone separation chamber and configured to induce a spiraling airflow within said chamber separates the entities from the airflow; and a first output for outputting at least a portion of the airflow substantially without entities;

a second output for outputting a second airflow carrying the entities, wherein the second output is connected to the entity presentation means.

5. The apparatus of claim 1 wherein said analyzing means comprises a computer having means for digital signal processing.

6. The apparatus of claim 1 wherein said tapered accelerating passageway has a length of about six inches, a diameter of about 0.5 inches on one end of said passageway, and a diameter of about 0.11 at the other end of said passageway.

7. An apparatus for sensing characteristics of elongate entities having length and width and carried in an airflow, at least a portion of the entities being in a looped condition in which an entity is folded back on itself along its length, comprising:

a sensing volume;

a tapered nozzle for receiving said entities in said airflow, accelerating said airflow and entities and presenting the entities in said sensing volume, said nozzle being dimensioned and configured to operate on and physically deloop about one-half or more of those entities that are received in a 100% looped condition and having a length greater than about 3 inches and a taper of less than about 3°;

sensor means for sensing the entities in said sensing volume and producing a sensor signal corresponding to characteristics of the sensed entities; and analyzing means for receiving and analyzing said sensor signal to produce output representing characteristics of the sensed entities.

8. The apparatus of claim 7 wherein said nozzle comprises:

said tapered nozzle having a length of about six inches;

said nozzle being tapered inwardly from an input to an output at a taper of less than three degrees (3°).

9. The apparatus of claim 7 wherein said nozzle is configured to optimally perform delooping at an airflow of about 1.3 CFM and to produce an airflow that exits the nozzle at a speed of about 100 m/sec.

10. An apparatus for sensing characteristics of elongate entities having length and width and being carried in an airflow, at least a portion of the entities being in a looped condition in which an entity is folded back on itself along its length; comprising:

a sensing volume;

entity presentation means including at least a tapered accelerating passageway having a length greater than about 3 inches and a taper of less than about 3° for receiving the entities and airflow and presenting the entities in said sensing volume, a portion of the entities being presented in said sensing volume in a looped condition and a portion of the entities being presented in said sensing volume not in a looped condition;

sensor means for sensing the entities in said sensing volume and for producing a sensor signal corresponding to characteristics of the sensed entities; and analyzing means for receiving and analyzing said sensor signal and for determining at least one characteristic of looped entities based on said sensor signal.

11. The apparatus of claim 10 wherein said analyzing means determines the width of the looped entities.

12. The apparatus of claim 10 wherein said analyzing means determines the length of the looped entity.

13. The apparatus of claim 10 wherein said analyzing means further comprises means for distinguishing between sensor signals corresponding to looped entities and sensor signals corresponding to not looped entities.

14. The apparatus of claim 10 wherein said sensor means comprises:

a source of light directed through said sensing volume and first and second photodetectors for sensing light extinguished by said entities in said sensing volume, said first and second photodetectors being positioned in a side-by-side spaced apart relationship with said second photodetector being positioned downstream of said first photodetector with reference to the airflow in said sensing volume, said first and second photodetectors for producing first and second sensor signals, respectively, each including waveforms corresponding to sensed characteristics of entities in said sensing volume; and wherein said analyzer means further comprises means for identifying the beginning and the end of first and second waveforms in said first and second sensor signals, respectively, corresponding to a sensed entity, comparing at least a portion of the first waveform to the second waveform and producing a compensated waveform that compensates for varying velocities along the length of the entity as the entity is sensed and for determining the lengths of the entity based upon said compensated waveform.

15. The apparatus of claim 10 wherein said sensor means comprises:

a source of light directed through said sensing volume and first and second photodetectors for sensing light extinguished by said entities in said sensing volume, said first and second photodetectors being positioned in a side-by-side spaced apart relationship with said second photodetector being positioned downstream of said first photodetector with reference to the airflow in said sensing volume said first and second photodetectors for producing first and second sensor signals, respectively, each including waveforms corresponding to sensed characteristics of entities in said sensing volume;

and wherein said analyzer means further comprises
means for identifying first and second waveforms
in the first and second sensor signals, respectively,
corresponding to a single entity, for dividing the first waveform into N equal segments, for cross-correlating each of said N segments to the second waveform to produce N correlations, based on said N correlations, for producing a compensated first waveform that compensates for varying velocities along the length of the entity as it was sensed, and for determining the length of the sensed entity based upon the compensated waveform 16. The apparatus of claim 10 wherein said analyzer means further comprises:

means for analyzing the compensated waveform to determine the time durations of the waveform corresponding to an unlooped portion of the sensed entity and to looped portions of the waveform; and means for sorting said compensated waveform to produce a sorted waveform in the form of a set of values ordered by their magnitude, producing a derivative waveform corresponding to the instantaneous slope of the sorted waveform, locating major peaks in the derivative waveform, and based on the position of the major peaks, determining the time duration of the sorted waveform corresponding to looped, unlooped and multiply looped sections of the sensed entity.

17. The apparatus of claim 10 wherein said analyzer means further comprises means for analyzing the sensor signal for identifying waveforms corresponding to entities for identifying sections of the waveform that correspond to looped, unlooped and multiply looped sections of the sensed entity, and based on the identified sections determining the length of the looped, unlooped and multiply looped section of the sensed entity.

18. An apparatus for sensing characteristics of elongate entities having length and width and being carried in an airflow, comprising:

a sensing volume;

entity presentation means including at least a tapered accelerating passageway having a length greater than about 3 inches and a taper of less than about 3° for receiving the entities and airflow and presenting the entities in said sensing volume;

sensor means for sensing the entities in said sensing volume and for producing a sensor signal corresponding to characteristics of the sensed entities;

said sensor means comprising a source of light directed through said sensing volume and first and second photodetectors for sensing entities in said sensing volume, said first and second photodetectors being positioned to sense at first and second volumes, respectively, positioned in said sensing volume in a side-by-side spaced apart relationship with the second volume being positioned downstream of the first volume with reference to the airflow in said sensing volume, said first and second photodetectors for producing first and second sensor signals, respectively, each including waveforms corresponding to sensed characteristics of entities in said sensing volume; and said analyzer means further comprising means for identifying the beginning and the end of first and second waveforms in said first and second sensor signals, respectively, corresponding to a sensed entity, comparing at least a portion of the first waveform to the second waveform and producing a compensated waveform that compensates for varying velocities of the entity as the entity is sensed.

19. The apparatus of claim 18 wherein said analyzing means further comprises means for dividing the first waveform into N equal segments, for cross-correlating each of said N segments to the second waveform to produce N correlations, and, based on said N correlations, for producing a compensated first waveform that compensates for varying velocities of the entity as it was sensed.

* * * * *